(12) United States Patent
Siddiqui

(10) Patent No.: US 9,212,159 B1
(45) Date of Patent: Dec. 15, 2015

(54) NITRATED AND AMINE-REACTED ASPHALTENES

(71) Applicant: KING FAHD UNIVERSITY OF PETROLEUM AND MINERALS, Dhahran (SA)

(72) Inventor: Mohammad Nahid Siddiqui, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/617,540

(22) Filed: Feb. 9, 2015

(51) Int. Cl.
  *C07D 333/76* (2006.01)
  *C10G 29/00* (2006.01)
  *C10G 31/00* (2006.01)

(52) U.S. Cl.
  CPC .............. *C07D 333/76* (2013.01); *C10G 29/00* (2013.01); *C10G 31/00* (2013.01)

(58) Field of Classification Search
  CPC ..................................................... C07D 333/76
  USPC ........................................................... 549/41
  See application file for complete search history.

(56) References Cited

U.S. PATENT DOCUMENTS

| | | |
|---|---|---|
| 4,622,047 A | 11/1986 | Bernasconi et al. |
| 4,755,276 A | 7/1988 | Lewis |
| 5,075,361 A | 12/1991 | Derosa et al. |
| 5,132,005 A | 7/1992 | Derosa et al. |
| 8,734,639 B2 | 5/2014 | Siskin et al. |
| 2004/0232042 A1 | 11/2004 | Mukkamala |
| 2008/0251418 A1 | 10/2008 | Francisco et al. |

FOREIGN PATENT DOCUMENTS

| | | |
|---|---|---|
| WO | 2008/124043 A1 | 10/2008 |
| WO | 2013/036095 A1 | 3/2013 |

OTHER PUBLICATIONS

Reinhold Rühl, "The German Bitumen Forum—Co-Operation in Partnership," 10 Pages.
George A. Olah, et al., "Electrophilic and Free Radical Nitration of Benzene and Toluene With Various Nitrating Agents," Proc. Natl. Acad. Sci. USA, vol. 75, No. 3, pp. 1045-1049, Mar. 1978, Chemistry.
Mohammad Nahid Siddiqui, "Exploring the Chemical Reactivity of Asphaltenes," Prepr. Pap.-Am. Chem. Soc., Div. Fuel Chem. 2009, 54(1), pp. 14-15.
Xiaoliang Ma, et al., "Estimating Reactivity of Asphaltenes by a Combination of Quantum Chemical Calculation and Statistic Analysis," Prepr. Pap.-Am. Chem. Soc., Div. Fuel Chem. 2004, 49 (1), pp. 61-62.
John W. Shirokoff, et al., "Characterization of the Structure of Saudi Crude Asphaltenes by X-Ray Diffraction," Energy & Fuels 1997 American Chemical Society, vol. 11, No. 3, pp. 561-565.

*Primary Examiner* — Taofiq A Solola
(74) *Attorney, Agent, or Firm* — Oblon, McClelland, Maier & Neustadt, L.L.P.

(57) ABSTRACT

A functionalized asphaltene. The functionalized asphaltene being a nitrated or an amine-reacted asphaltene. The nitrated asphaltene, containing a fused polycyclic core, prepared by reacting an asphaltene with nitric acid, wherein a first nitrate is attached to an aromatic ring of a dibenzothiophene group, and a second nitrate is attached to an aromatic ring of a benzoanthracene group of the asphaltene to obtain a nitrated asphaltene. The amine-reacted asphaltene prepared by reacting an asphaltene, containing a fused polycyclic core, with amines; wherein a first alkyl or aryl group is attached to an aromatic ring of a dibenzothiophene group of the asphaltene, and a second alkyl or aryl group is attached to an aromatic ring of a benzoanthracene group of the asphaltene.

19 Claims, 18 Drawing Sheets

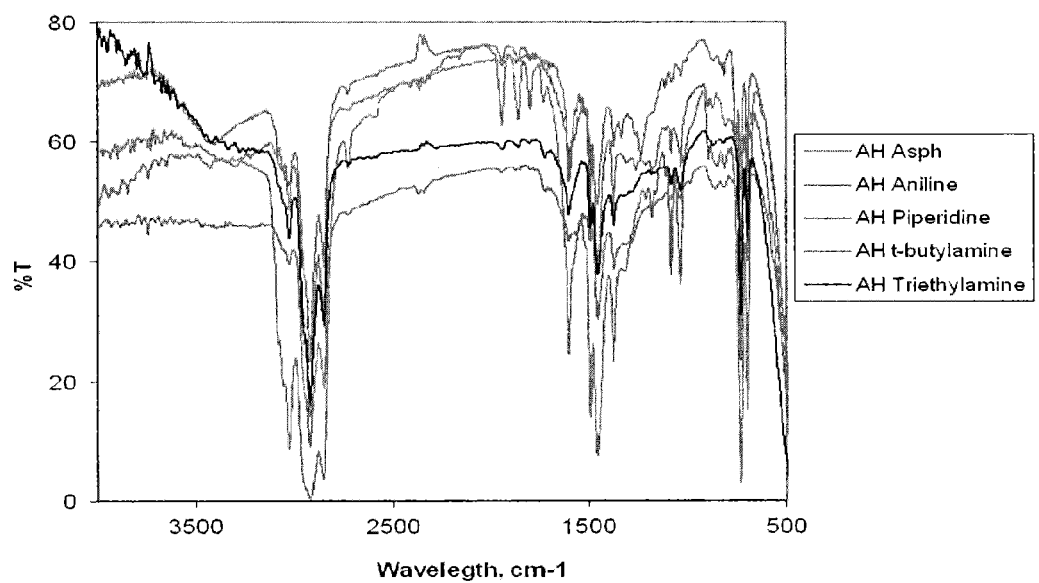
Figure 1 IR spectra of Reactions of amines with AH asphaltene

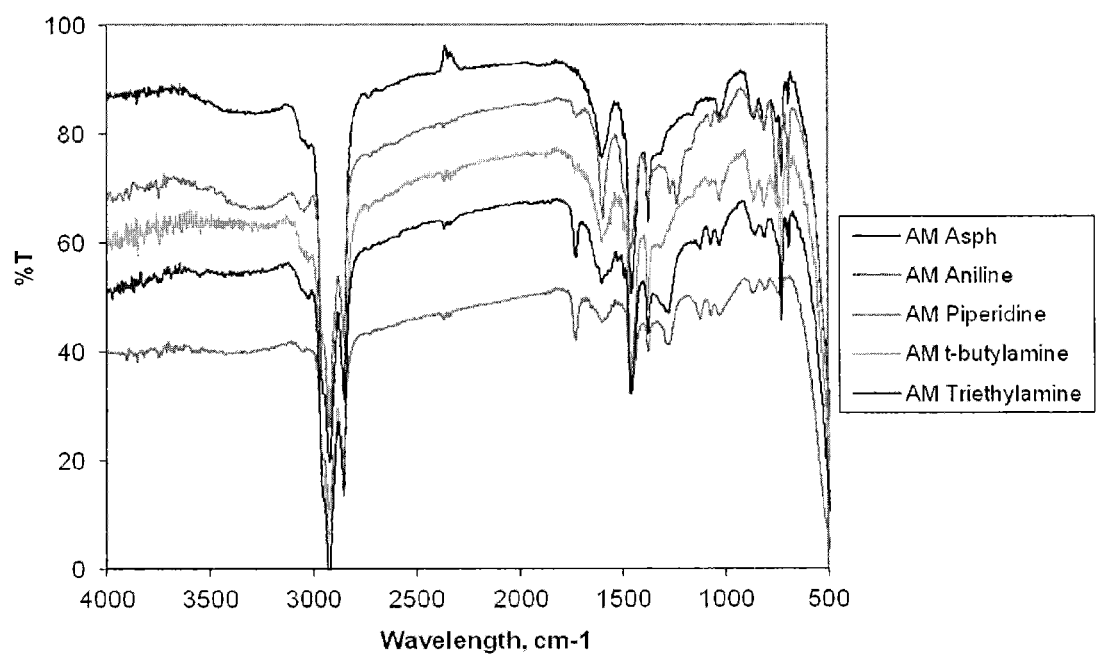
Figure 2 IR spectra of Reactions of amines with AM asphaltene

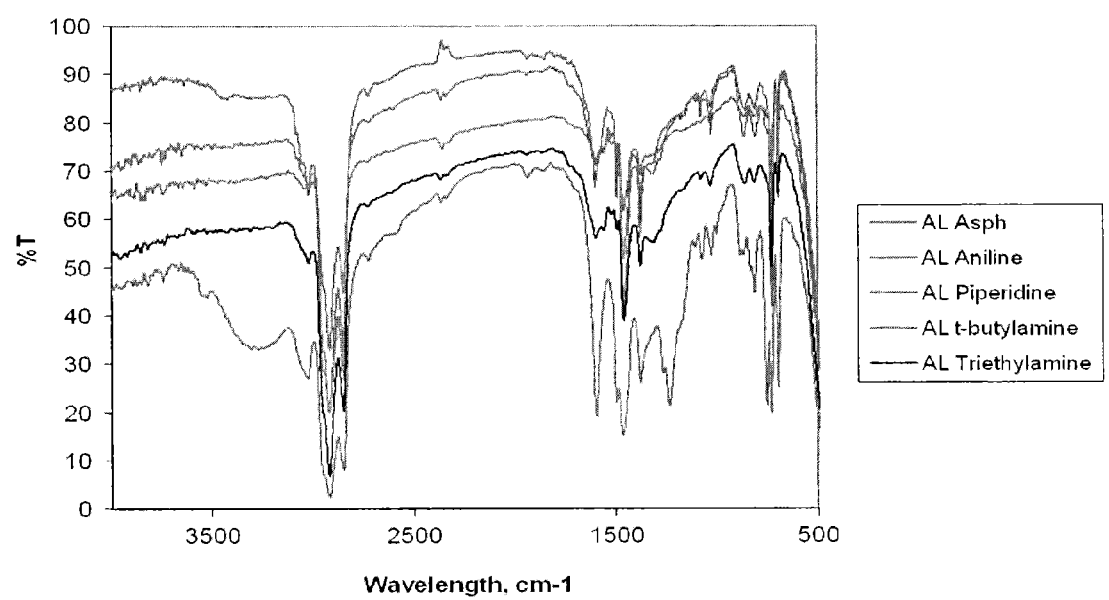
Figure 3 IR spectra of Reactions of amines with AL asphaltene

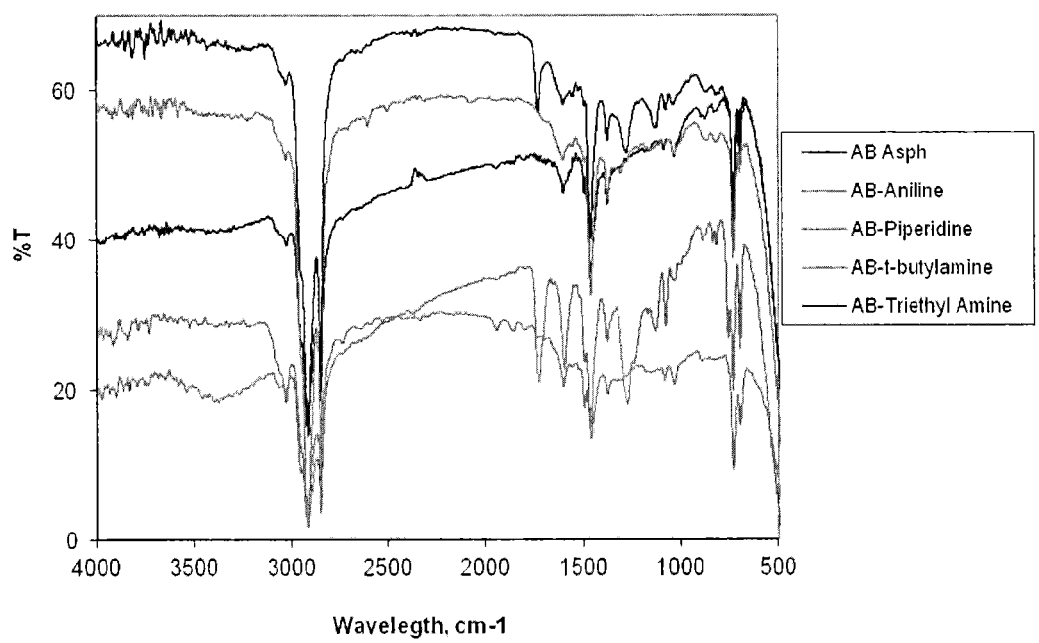
Figure 4 IR spectra of Reactions of amines with AB asphaltene

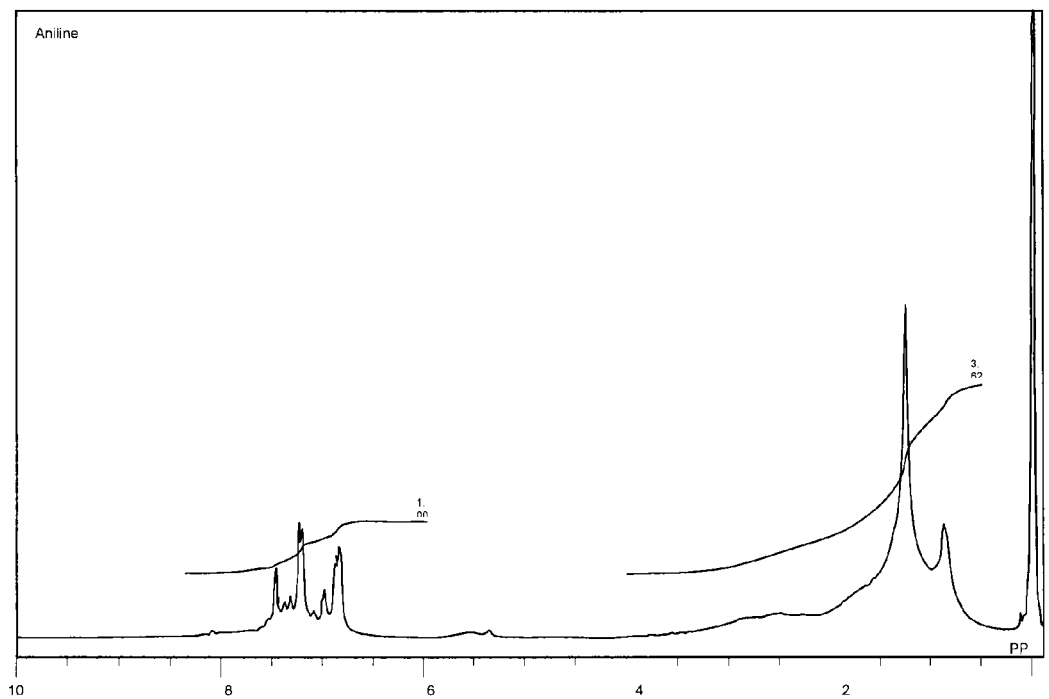
Figure 5 Proton NMR spectra of AH asphaltenes after reacting with aniline

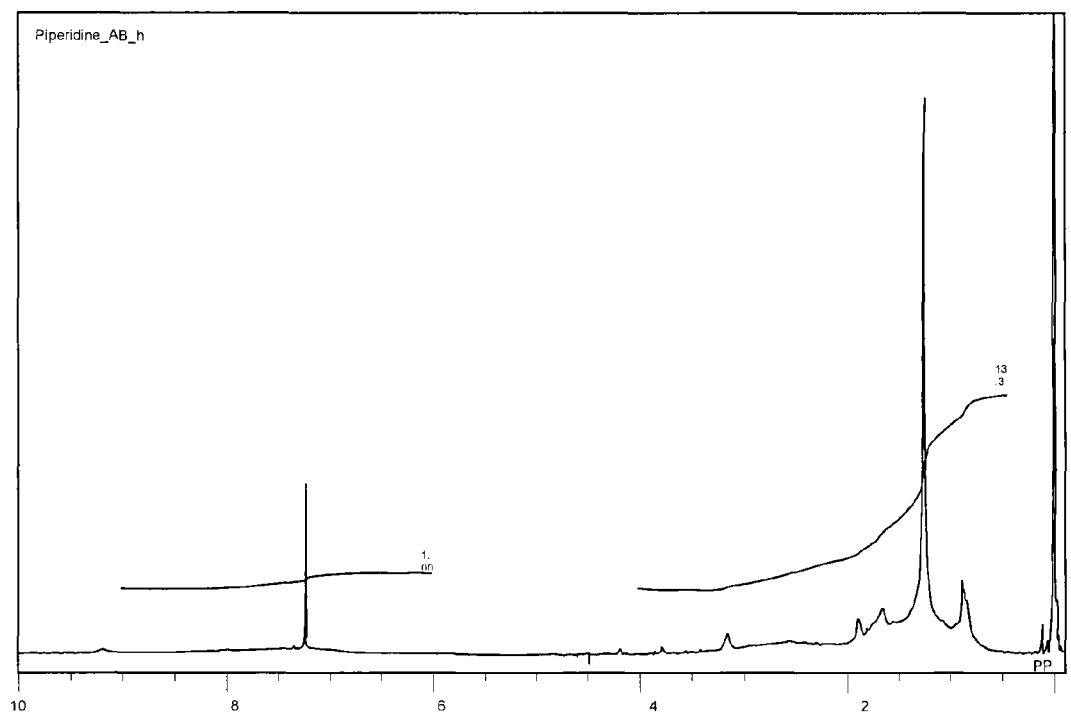
Figure 6 Proton NMR spectra of AB asphaltenes after reacting with piperidine

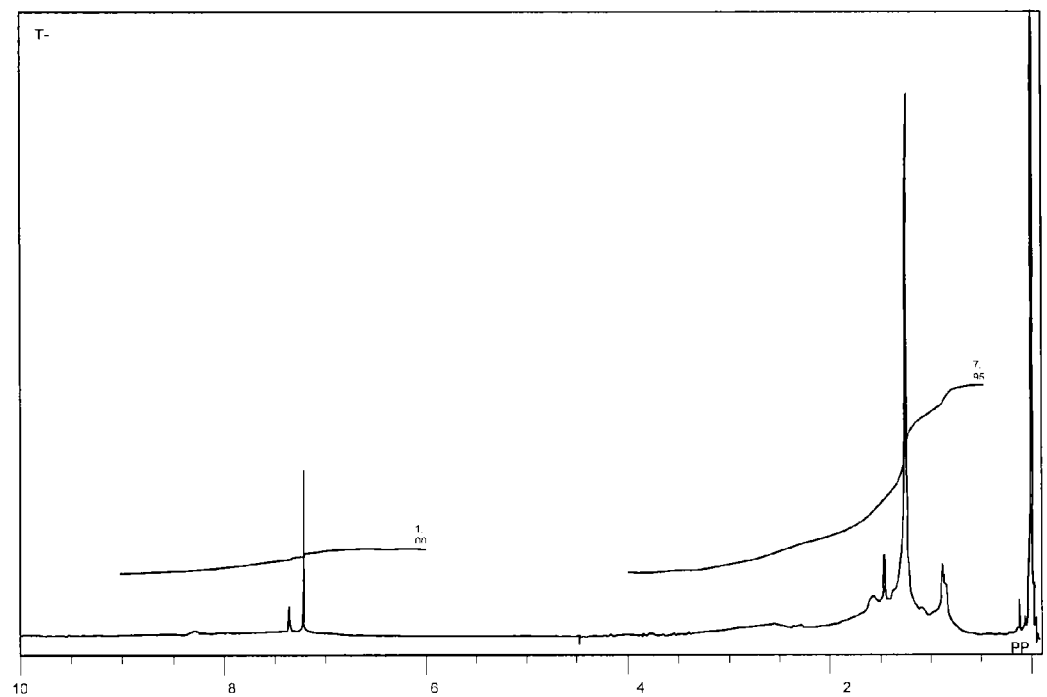
Figure 7 Proton NMR spectra of AB asphaltenes after reacting with t-butylamine

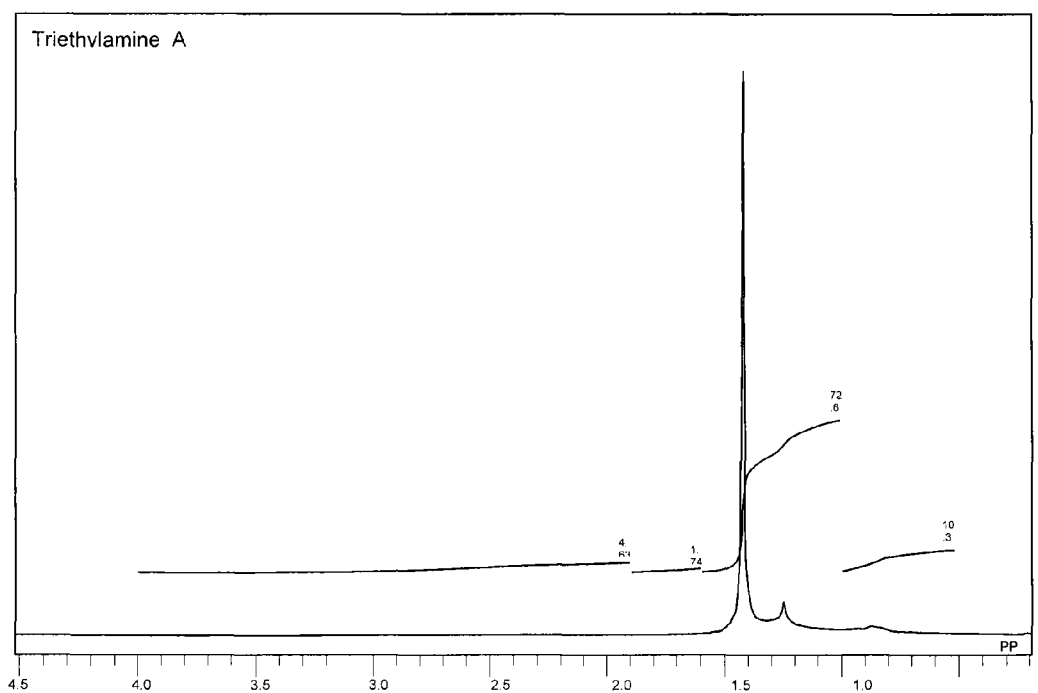
Figure 8 Proton NMR spectra of AL asphaltenes after reacting with triethylamine

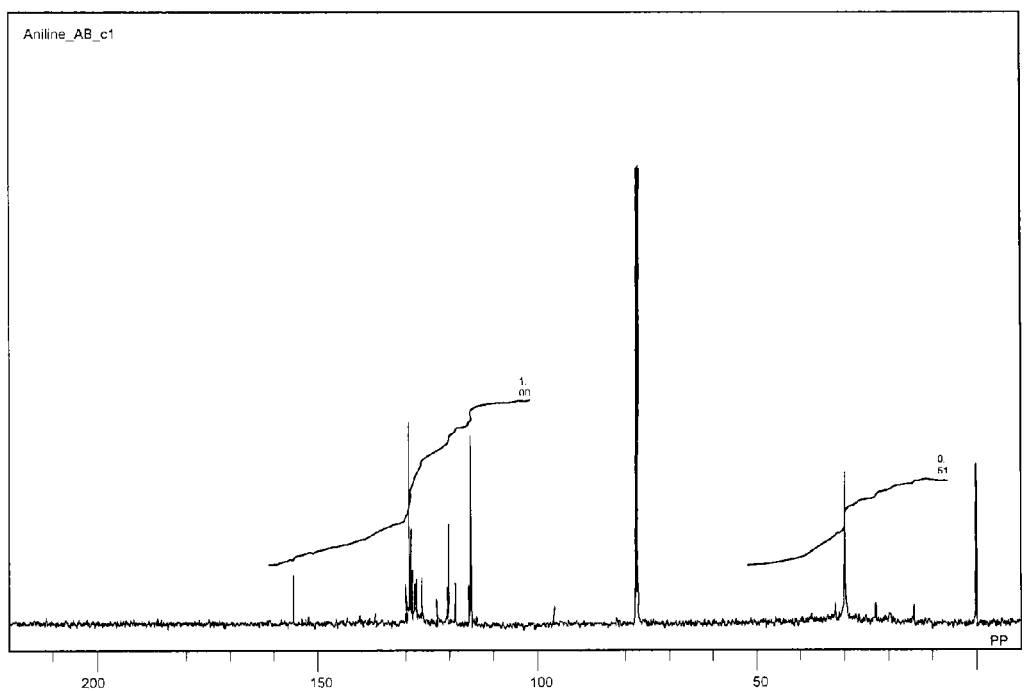
Figure 9 Carbon NMR spectra of AB asphaltenes after reacting with aniline

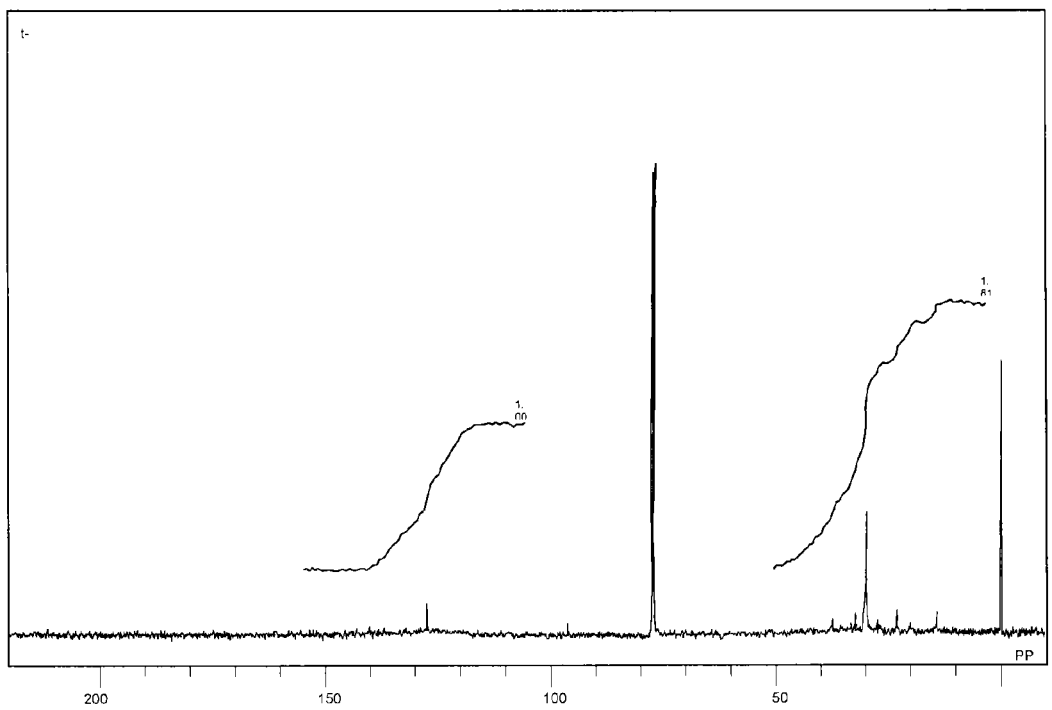
Figure 10 Carbon NMR spectra of AL asphaltenes after reacting with t-butylamine

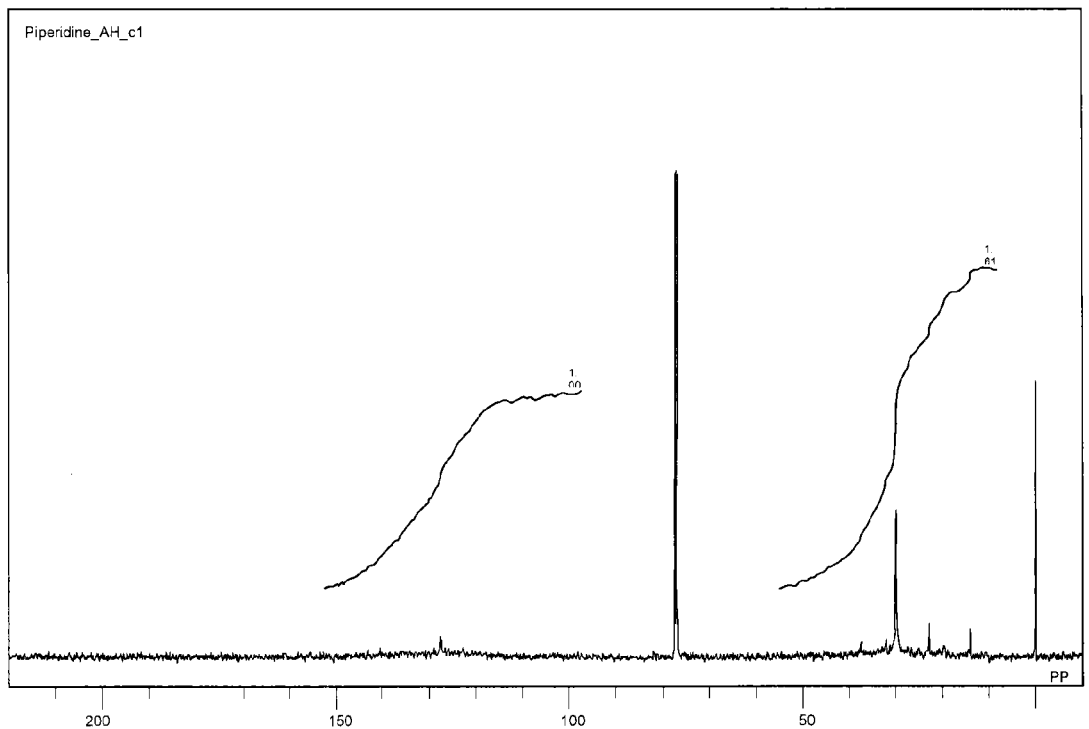
Figure 11 Carbon NMR spectra of AH asphaltenes after reacting with piperidine

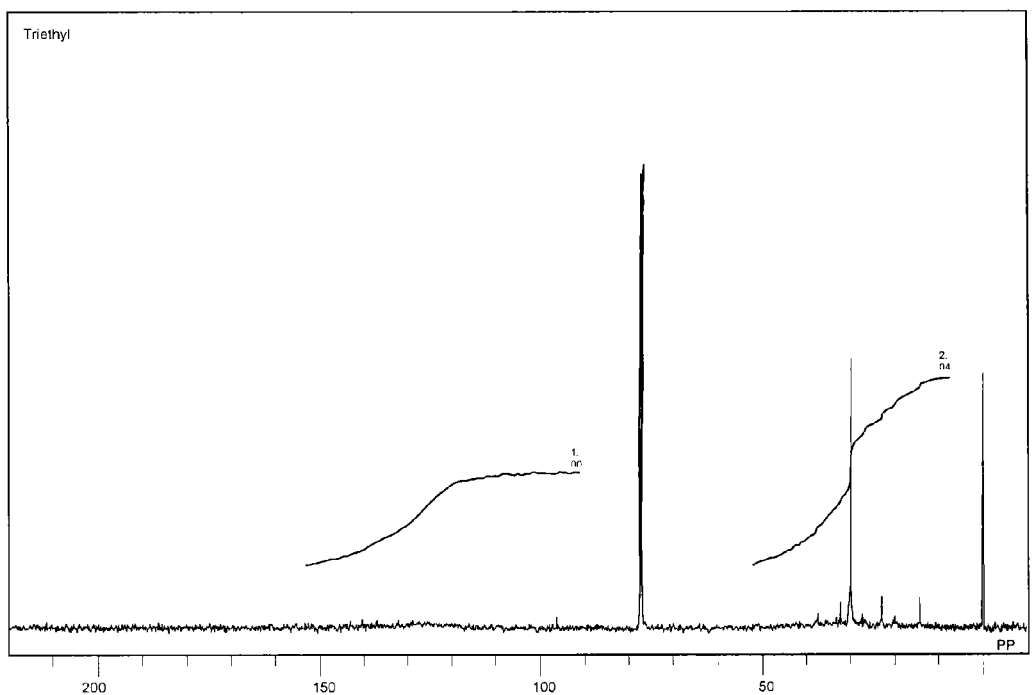
Figure 12 Carbon NMR spectra of AB asphaltenes after reacting with triethylamine

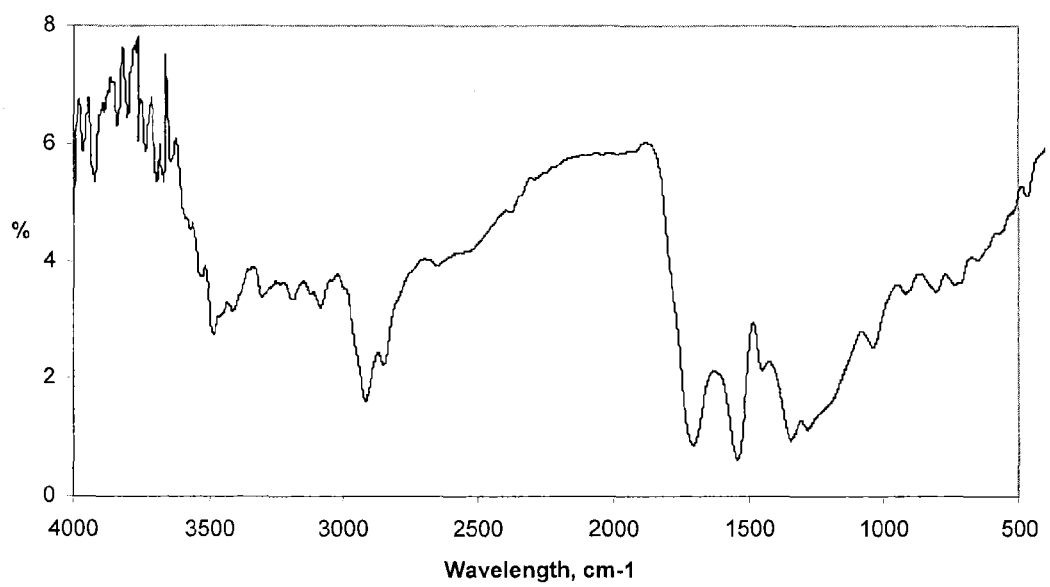
Figure 13 IR spectra of AH asphaltenes after nitration

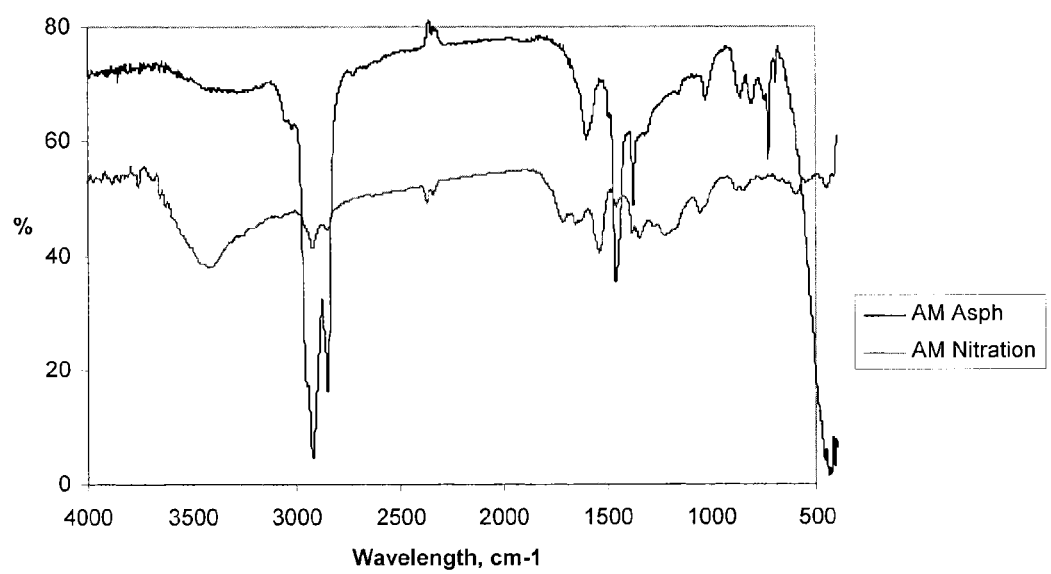
Figure 14 IR spectra of AM asphaltenes after nitration

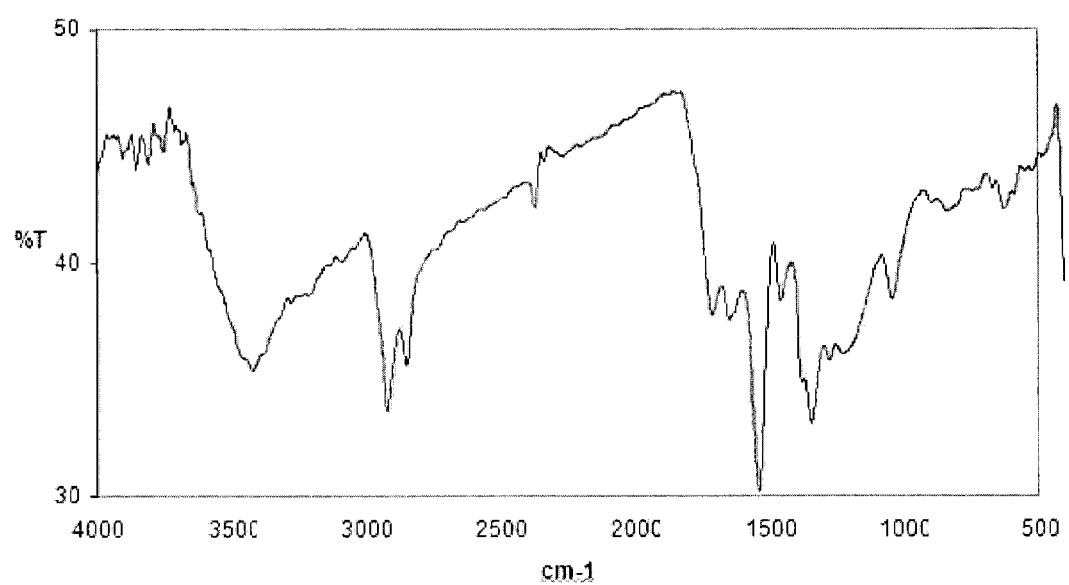
Figure 15 IR spectra of AL asphaltenes after nitration

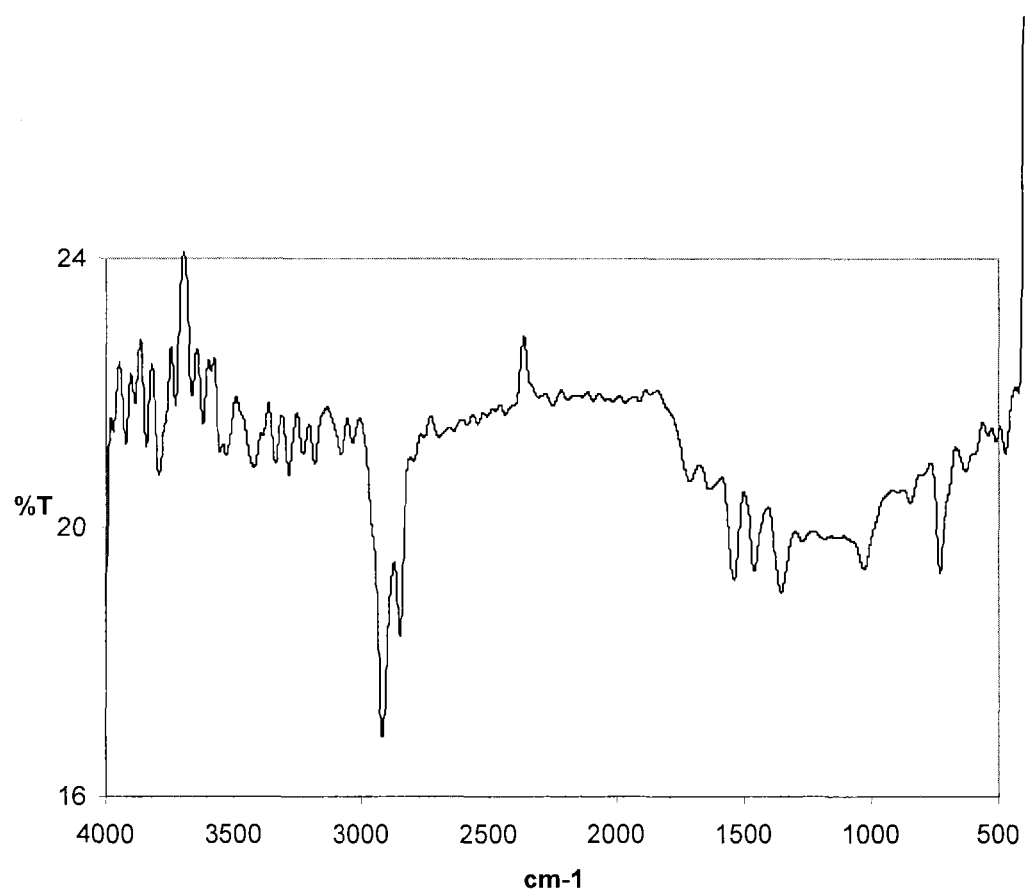
Figure 16 IR Spectra of AB asphaltenes after nitration

Figure 17 Proton NMR spectra of AL asphaltenes after nitration
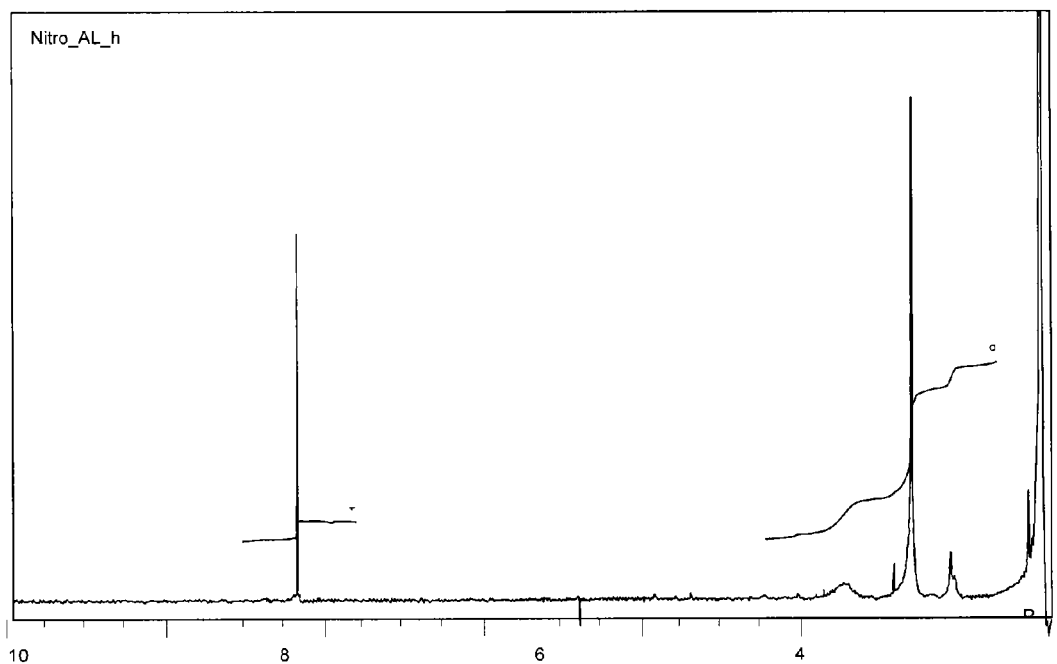

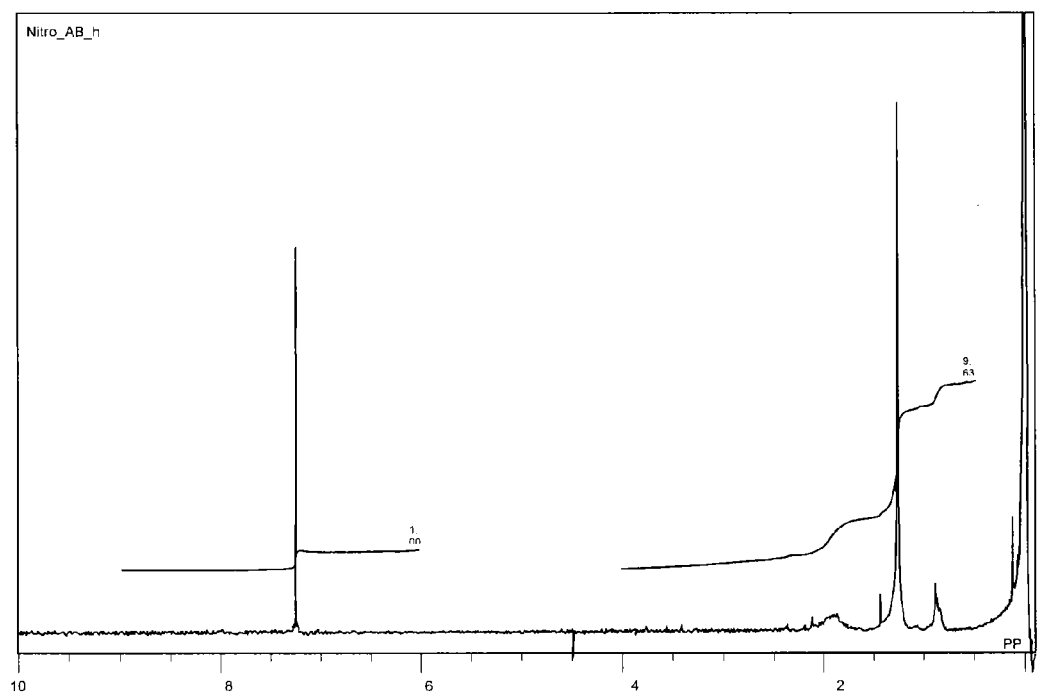
Figure 18 Proton NMR spectra of AB asphaltenes after nitration

NITRATED AND AMINE-REACTED ASPHALTENES

BACKGROUND OF THE INVENTION

1. Technical Field

The present disclosure is directed to nitrated and amine-reacted derivatives of asphaltenes. The disclosure includes a process for reacting a nitrating agent with an asphaltene to form a nitrated asphaltene. The disclosure also includes a process for reacting an amine with an asphaltene to form an alkylated or arylated asphaltene.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Petroleum heavy residue conversion processes are increasingly important in the petrochemical industry due to market and economic factors. In the future, it is projected that the petroleum industry will increase its reliance on much heavier crude oil supplies. The increased heavy crude oil feedstock supply availability will further result in increasing yields of low value refinery residues, such as residual fuel oil and coke. Depending on the nature of crude oil, these refinery residues can present up to about 60% of the original crude oil. The residue of heavy crude oils can be upgraded [Lepage, J. F.; Chatila, S. G.; Davidson, M. In *Residue and Heavy Oil Processing*; Editions Technip: Paris, 1992. Incorporated herein by reference in its entirety].

One of the challenges the petroleum industry faces with upgrading residues is how to handle a molecular substance known as an asphaltene. Asphaltenes are components of crude oil that are present in all of the petroleum processing phases. Although found in insignificant quantities, they are nonetheless one of the most notable compounds present in petroleum due to their precipitation and flocculation properties. Asphaltenes can also increase the viscosity of oil, which can in turn reduce, or even halt, its flow. Furthermore, asphaltenes are known to be coke precursors in acid catalysis and can act as catalyst inhibitors by catalyst deactivation and catalyst poisoning. As such, asphaltenes pose a serious problem to a variety of processes in the petroleum industry.

Generally, there are two main approaches in dealing with asphaltenes during the oil processing phases. Foremost, it can be deemed advantageous to maintain asphaltenes in a stable suspension in a crude oil liquid until well into the petroleum refining process. The ability to keep asphaltenes stable in the liquid results in higher production yields, and furthermore, a decrease or elimination of maintenance problems to industry equipment. This may be accomplished by the addition of a chemical group to the polycyclic core of an asphaltene, thus creating a functionalized asphaltene, in order to increase its solubility. Alternatively, the ability of asphaltenes to flocculate can be used to the industry's advantage, wherein an increased precipitation of asphaltenes, and their subsequent removal, will result in a less viscous petroleum feed stream. This may be accomplished by the addition of chemical groups to the polycyclic core of an asphaltene, thus creating a functionalized asphaltene, in order to decrease its solubility. Therefore, the reactivity behavior of asphaltenes is vital towards understanding the functional properties of asphaltenes to form aggregates, micelles, and coke in a variety of refining and upgrading processes of the petroleum industry.

On the molecular level, asphaltenes are composed of various chemical species. Asphaltenes have a low hydrogen to carbon (H/C) ratio, and are believed to possess several long paraffinic side chains as opposed to many shorter paraffinic side chains or naphthenic groups. Subsequently, they are known to be polar and insoluble in a paraffinic solvent. Furthermore, asphaltenes cannot crystallize and cannot be separated individually. The condensed structural units of asphaltenes bear alicyclic sites substituted and connected to aliphatic chains, with or without heteroatoms. Asphaltenes also include a heterogeneous mixture of highly polydispersed molecules, in terms of size and chemical composition, with a high content of heteroatoms (S, N, O) and metals (Ni and V) [Hasan, M.; Siddiqui, M. N. and Arab, M.; *Oil and Gas Journal*, 1988a, February 8, 38-40. Hasan, M.; Siddiqui, M. N. and Arab, M.; *Fuel*, August 1988b, Vol. 67, No. 8, 1131-1134. Incorporated herein by reference in their entirety].

Asphaltenes, depending on the source of crude oil, contain a variety of polycyclic aromatic hydrocarbons at their core. Several hundred polycyclic aromatic hydrocarbons have been identified in petroleum substances, such as asphalt. Also known as polyaromatic hydrocarbons, these organic compounds are composed of multiple aromatic rings in which the electrons are delocalized. Although poly signifies 'many', there is precedence in the nomenclature to refer to two-ring cases as biphenyl and naphthalene, while anthracene and phenanthrene are examples of three-ringed structures.

For Saudi crude oil, the asphaltene content characterized by condensed aromatic systems carrying alkyl, cycloalkyl and heteroatom constituents, has an average layer distance between aromatic sheets that measures approximately 3.6 Å. The average interchain layer distance is between 4.4 and 4.5 Å, and the average stack height of the aromatic sheets perpendicular to that plane of the sheets ranges between 22.7 and 24.7 Å. X-ray diffraction studies of the four Saudi crude oil asphaltenes support the concept of condensed aromatic sheets having a tendency to stack, bearing naphthenic and alkyl systems on their periphery [Shirokoff, John W., Siddiqui, Mohammad N., Ali, Mohammad F., Characterization of the Structure of Saudi Crude Asphaltenes by X-ray Diffraction, *Energy & Fuels* 1997, 11, 561-565 Incorporated herein by reference in its entirety].

Arab Berri asphaltene is found to possess the highest estimate of aromaticity followed by Arab Light and Arab Heavy, whereas Arab Medium is considered the lowest in aromaticity. Sulfur content decreases from Arab Heavy to Arab Medium to Arab Light and Arab Berri having equivalent amounts. Oxygen content increases from Arab Heavy to Arab Light to Arab Medium to Arab Berri. [Shirokoff, John W., Siddiqui, Mohammad N., Ali, Mohammad F., Characterization of the Structure of Saudi Crude Asphaltenes by X-ray Diffraction, *Energy & Fuels* 1997, 11, 561-565 Incorporated herein by reference in its entirety].

Bridgehead carbons, which serve to connect different rings within the same molecule, vary in comparison of the four Saudi crude asphaltenes. However, this parameter can be used to indicate the extent of compactness and ring condensation. [Shirokoff, John W., Siddiqui, Mohammad N., Ali, Mohammad F., Characterization of the Structure of Saudi Crude Asphaltenes by X-ray Diffraction, *Energy & Fuels* 1997, 11, 561-565 Incorporated herein by reference in its entirety].

As the petroleum industry looks for ways to increase yield from heavy crude oil fractions, attention has turned to studies involving the chemical reactivity of asphaltenes. For example, several studies have reported on the reductive and non-reductive alkylation of asphaltenes using different type of reagents. [Speight, J. G and R. J. Pancirov, R. J.; Preprints, Am. Chem. Soc., Div. Petrol. Chem. 28 (1983), p. 1319; Ali, M. F., Siddiqui, M. N. and Al-Hajji A. A., *Petroleum Science & Technology,* 2004, 22(5 & 6), p. 655; Cagniant, D.; Nosyrev, I.; Cebolla, V.; Vela, J.; Membrado, L. and Gruber, R.; *Fuel,* 2001, 80(1), 107. Incorporated herein by reference in their entirety].

Acevedo et al. have carried out the synthesis and isolation of octylated asphaltenes for the determination of more realistic molecular weight distributions of asphaltenes [Acevedo, S.; Escobar, G.; Ranaudo, M. A. and Rizzo, A.; *Fuel,* 1998, 77(8), 853 Incorporated herein by reference in its entirety]. Friedel-Crafts alkylation and potassium permanganate oxidation of Arab heavy and Arab medium asphaltenes have also been carried out to understand the chemical reactivity of asphaltenes. [Siddiqui, M. N. *Fuel,* 2003, 82(11), p. 1323 Incorporated herein by reference in its entirety]. The hydrogen bonding capacities of four Saudi Arabian crude-oil-derived asphaltenes against the phenol and piperidine solutions of various concentrations in carbon tetrachloride has also been explored. [Siddiqui, M. N., *Petroleum Science & Technology,* 2003, 21(9-10), p. 1601. Incorporated herein by reference in its entirety]. The chlorination reaction of asphaltenes has been disclosed as well. [Siddiqui Prepr. Pap.-Am Chem. Soc., Div. Fuel Chem 2009, 54(1), 14 Incorporated herein by reference in its entirety].

Therefore, in order to study the reactivity behavior, an asphaltene may be functionalized by the addition of a chemical group to its polycyclic core, or to a paraffinic side chain.

BRIEF SUMMARY OF THE INVENTION

According to a first embodiment, the present invention relates to a functionalized asphaltene comprising a polycyclic aromatic core, at least one dibenzothiophene group and at least one benzoanthracene group where at least one of the dibenzothiophene groups is nitrated at an aromatic group and/or at least one of the benzoanthracene groups is nitrated at an aromatic group.

In a further embodiment the functionalized asphaltene includes a benzoanthracene group which is 1H-benzo[de]anthracene.

In a further embodiment the functionalized asphaltene comprises a polycyclic aromatic core containing at least one 2-methyldibenzo[b,d]thiophene group.

In a further embodiment the functionalized asphaltene comprises a polycyclic aromatic core containing at least one (cyclopentylmethyl) (2,3,4,5,6-pentamethylphenyl) sulfane group.

In a further embodiment the disclosure includes a method of preparing the functionalized asphaltene by selectively substituting polar substituents onto the polycyclic aromatic core of an asphaltene by an electrophilic aromatic substitution reaction through the formation of a nitronium ion with a nitrating agent and a Lewis acid catalyst to yield nitronium.

In a further embodiment the electrophilic aromatic substitution reaction is nitration.

In a further embodiment the electrophilic aromatic substitution reaction takes place at a temperature maintained between 5° C. and 15° C.

In a further embodiment the source of the functionalized asphaltenes is Saudi crude oil wherein the Saudi Crude Oil is selected from the group consisting of Arabia Extra Light (AB), Arabian Light (AL), Arabian Medium (AM) and Arabian Heavy (AH).

In a further embodiment the disclosure includes a method for upgrading heavy hydrocarbon feed streams by either the removal therefrom of functionalized asphaltenes, wherein the selective substitution renders the thus substituted asphaltenes less soluble in the heavy hydrocarbon feed stream resulting in precipitation, and separating the precipitate from the heavy hydrocarbon feed stream, or wherein the selective substitution renders the thus substituted asphaltenes more soluble in the heavy hydrocarbon feed stream, resulting in their solubilization.

According to a second embodiment, the present invention relates to a functionalized asphaltene comprising a polycyclic aromatic core, at least one dibenzothiophene group and at least one benzoanthracene where at least one dibenzothiophene group is alkylated or arylated at an aromatic group and at least one of the benzoanthracene groups is alkylated or arylated at an aromatic group.

In a further embodiment the functionalized asphaltene includes a benzoanthracene group which is 1H-benzo[de]anthracene.

In a further embodiment the functionalized asphaltene comprises a polycyclic aromatic core containing at least one 2-methyldibenzo[b,d]thiophene group.

In a further embodiment the functionalized asphaltene also comprises a polycyclic aromatic core containing at least one (cyclopentylmethyl) (2,3,4,5,6-pentamethylphenyl) sulfane group.

In a further embodiment the disclosure includes a method of preparing the functionalized asphaltene by selectively substituting alkyl or aryl substituents onto the polycyclic aromatic core of an asphaltene by initially forming a diazonium salt via the reaction of nitrous acid with aniline in an acidic solution and subsequently reacting the diazonium salt with various amines.

In a further embodiment the functionalized asphaltene is reacted with a primary, secondary, or tertiary amine.

In a further embodiment directed to the method of preparing the functionalized asphaltenes of our second embodiment wherein the amine is selected from the group consisting of aniline, piperidine, t-butyl amine, or triethyl amine.

In a further embodiment the alkyl- or aryl-substitution reaction takes place at a temperature maintained between 5° C. and 15° C.

In a further embodiment the disclosure includes a method for upgrading heavy hydrocarbon feed streams by either the removal therefrom of functionalized asphaltenes, wherein the selective substitution renders the thus substituted asphaltenes less soluble in the heavy hydrocarbon feed stream resulting in precipitation, and separating the precipitate from the heavy hydrocarbon feed stream, or wherein the selective substitution renders the thus substituted asphaltenes more soluble in the heavy hydrocarbon feed stream resulting in their solubilization.

In a further embodiment the source of the functionalized asphaltenes is Saudi Crude Oil wherein the Saudi Crude Oil is selected from the group consisting of Arabia Extra Light (AB), Arabian Light (AL), Arabian Medium (AM) and Arabian Heavy (AH).

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 shows an overlaid IR spectrum of AH asphaltene after reacting with different amines.

FIG. 2 shows an overlaid IR spectrum of AM asphaltenes after reacting with different amines.

FIG. 3 shows an overlaid IR spectrum of AL asphaltenes after reacting with different amines.

FIG. 4 shows an overlaid IR spectrum of AB asphaltenes after reacting with different amines.

FIG. 5 shows proton NMR spectra of AH asphaltenes after reacting with aniline.

FIG. 6 shows proton NMR spectra of AB asphaltenes after reacting with piperidine.

FIG. 7 shows proton NMR spectra of AB asphaltenes after reacting with t-butylamine.

FIG. 8 shows proton NMR spectra of AL asphaltenes after reacting with triethylamine.

FIG. 9 shows carbon NMR spectra of AB asphaltenes after reacting with aniline.

FIG. 10 shows carbon NMR spectra of AL asphaltenes after reacting with t-butylamine.

FIG. 11 shows carbon NMR spectra of AH asphaltenes after reacting with piperidine.

FIG. 12 shows Carbon NMR spectra of AB asphaltenes after reacting with triethylamine.

FIG. 13 shows the IR spectra of AH asphaltenes after nitration.

FIG. 14 shows the IR spectra of AM asphaltenes after nitration.

FIG. 15 shows the IR spectra of AL asphaltenes after nitration.

FIG. 16 shows the IR spectra of AB asphaltenes after nitration.

FIG. 17 shows the proton NMR spectra of AL asphaltenes after nitration.

FIG. 18 shows the proton NMR spectra of AB asphaltenes after nitration.

DETAILED DESCRIPTION OF THE EMBODIMENTS

One aspect of the invention includes a functionalized asphaltene. Asphaltene molecules contain fused polyaromatic rings forming a polycyclic core which can include heteroatoms such as sulfur, oxygen, and nitrogen. These heteroatoms may be part of the aromatic ring system or part of other carbocyclic rings, linking groups, or functional groups. In the structural motif known as the continental structure, alkyl chains connect to and branch from a central polyaromatic ring system. In an alternative archipelago structural motif, multiple polyaromatic ring systems are connected by alkyl chains that may contain a heteroatom, and additional alkyl chains extend freely from the polyaromatic rings. The number of fused aromatic rings in the continental structure can be greater than the number of fused aromatic rings in the archipelago structure.

In addition to the aromatic regions of the asphaltenes, heteroatoms provide the asphaltenes with polar regions, and the terminal alkyl chains provide hydrophobic regions. As a result of these polar and non-polar regions, it is believed that asphaltene molecules aggregate into various micellular structures in oil, with the alkyl chains interacting with the aliphatic oil components. Furthermore, asphaltenes can precipitate from oil in structures where asphaltene molecules form stacked layers having aligned aromatic regions and aligned aliphatic regions. The nitration of an asphaltene, resulting in the formation of a functionalized asphaltene, will therefore influence the aggregate properties of asphaltenes. Likewise, the addition of alkyl or aryl groups to an asphaltene, resulting in the formation of a functionalized asphaltene, will also influence the aggregate properties of asphaltenes.

As used herein, a 'polycyclic core' refers to a part of a molecule comprising at least two hydrocarbon ring structures either fused together or linked via a single or double bond. Fused means that the hydrocarbon ring structures have at least one bond in common. As used herein, the ring may be a 5- or 6-membered carbon-based structure. Hence, all of the ringed structures of a polycyclic core do not need to comprise the same number of atoms. Although the majority of atoms forming the rings are carbon, other atoms may be chosen from the group containing N, O, or S. Additionally, in most cases, all of the atoms forming the ring may be carbon. Each of the rings of the polycyclic core may bear one or more substituents. Non limiting examples of such substituents include alkyl and aryl compounds.

Aliphatic compounds are organic compounds in which carbon atoms are joined together in a straight or branched chain or in rings. These compounds may be either saturated or unsaturated, but not aromatic. Therefore, aliphatic is a non-aromatic moiety.

The asphaltenes found in Saudi crude oils include several specific polyaromatic rings and aromatic heteroatom-substituted groups, herein described, but not limited to: benzoanthracene, such as 1H-benzo[de]anthracene; dibenzothiophene, such as 2-methyldibenzo[b,d]thiophene; (cyclopentylmethyl) (2,3,4,5,6-pentamethylphenyl) sulfane, benzo[b]naphtho[1,2-d]thiophene, and 1,2,4,5,7-pentamethyl-8-propyl-1,2,3,4-tetrahydronaphthalene.

Benzoanthracenes ($C_{12}H_{18}$) are a series of compounds containing four fused benzene rings. Benzoanthracenes contain an anthracene core fused to a further benzene group. Benzoanthracenes can be substituted or un-substituted with one or more alkyl, aryl or heteroatom-containing hydrocarbon groups such as hydroxyl, acyl, alkoxy and related sulfur compounds. They are members of the polycyclic aromatic hydrocarbon (PAH) family. 3,4-Benz[a]anthracene and 1H-benzo[de]anthracene (1) are members of the benzoanthracene series, and furthermore, a four-ringed member of the series of acenes.

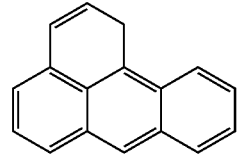

(1)

Dibenzothiophenes are organosulfur compounds containing two benzene rings fused to a central thiophene ring. Also known as a tricyclic heterocycle, it is commonly seen as a component of heavier fractions of petroleum. A methyl-substituted dibenzothiophene, known as 2-methyldibenzo[b,d]thiophene (2), may be present in the asphaltene structure of the Saudi crude oils. Benzothiophenes may alternately be substituted with one or more other $C_1$-$C_{24}$ alkyl or aryl groups including ethyl, ethyl, propyl, butyl, pentyl and hexyl.

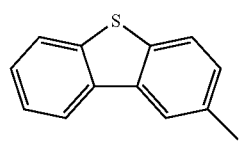

(2)

One or more aryl sulfane groups containing at least one aryl group and preferably an aryl group and an aliphatic or alicyclic group may also be present as a substituent of an asphaltene. For example, cyclopentylmethyl 2,3,4,5,6-pentamethylphenyl sulfane (3) is a sulfur containing moiety that may be positioned on the periphery of the polycyclic core of an asphaltene. The sulfur atom may also be considered a reactive site.

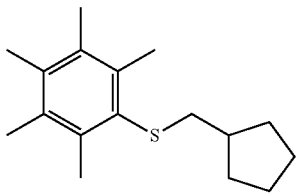

(3)

Additional chemical groups, such as 1,2,4,5,7-pentamethyl-8-propyl-1,2,3,4-tetrahydronaphthalene (4) may also be present as part of the polycyclic core structure of asphaltenes obtained from Saudi crude oil, and may furthermore, be reactive in nitration, as well as alkylation and arylation reactions. This compound is an aromatic bicyclic hydrocarbon of the series of acenes.

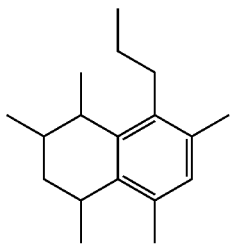

(4)

The structure of an asphaltene (8) according to one or more alternative embodiments of the invention is shown and comprises a 1H-benzo[de]anthracene ring fused to a 2-methyldibenzo[b,d]thiophene ring. A 1,2,4,5,7-pentamethyl-8-propyl-1,2,3,4-tetrahydronaphthalene group is furthermore attached to the 1H-benzo[de]anthracene ring at the 8-position to give 8-1,2,4,5,7-pentamethyl-8-propyl-1,2,3,4-tetrahydronaphthalene-1H-benzo[de]anthracene. Additionally, the cyclopentylmethyl 2,3,4,5,6-pentamethylphenyl sulfane group is fused to the 1H-benzo[de]anthracene ring, and, furthermore, the 2-methyldibenzo[b,d]thiophene ring is fused with a 1-hexyl-2,3,4,5,6-pentamethyl-1,2,3,4-tetrahydronaphthalene group (5).

(5)

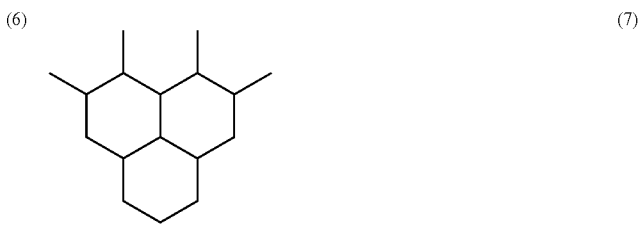

This group (5) is not considered to be reactive in nitration, or alkylation/arylation reactions that occur on the asphaltene.

Alkyl and aryl moieties may be fused to the 1H-benzo[de]anthracene, such as 2-hexyl-1,3-dimethylcyclohexane (6), and 1,2,8,9-tetramethyldodecahydro-1H-phenalene (7). These groups are not considered to be reactive in the nitration, nor alkylation/arylation reactions.

(6)

(7)

(8)

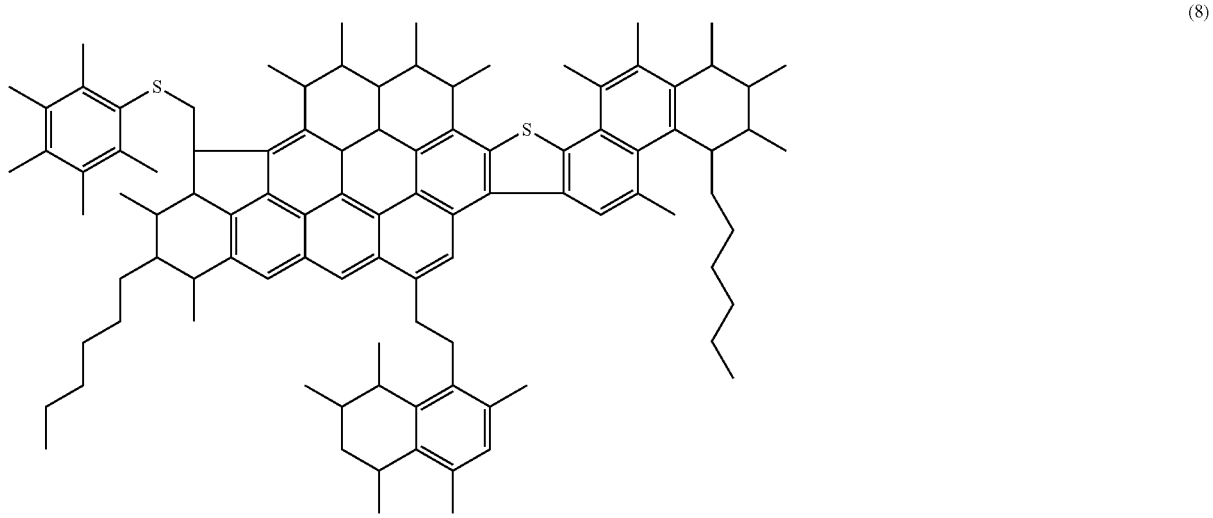

Based upon the location of these ringed compounds on or in the polycyclic core of the asphaltene molecule, nitration and alkylation/arylation reactions will take place on at least one of the benzoanthracene rings, and/or on least one of the dibenzothiophene rings to form a functionalized asphaltene. Nitration and alkylation/arylation reactions may also take place on the cyclopentylmethyl 2,3,4,5,6-pentamethylphenyl sulfane structure (3) as well as the 1,2,4,5,7-pentamethyl-8-propyl-1,2,3,4-tetrahydronaphthal ene structure (4), to further functionalize the asphaltene.

In further detail, one aspect of the present invention is directed toward the reaction of asphaltenes from Saudi crude oil residues with aromatic, tertiary, aliphatic and heterocyclic amines, and more specifically to the reaction of asphaltenes with aniline, triethyl amine, t-butyl amine, and piperidine. The reaction of asphaltenes with aniline, triethyl amine, t-butyl amine, and piperidine exhibited various degrees of reactions. These initial amine-reacted asphaltenes by themselves, or with further modification, can affect asphaltene reactivity, and thus are useful to the petroleum industry. Additional amines, given as $RNH_2$, can include, but are not limited to, methylamine, ethanolamine, and tris(hydroxymethyl)aminomethane (TRIS).

Amines are weak bases and may be regarded as organic substitution products of ammonia. Just as ammonia reacts with acids to form the ammonium ion, so the amines react with acid to form the organoammonium ions. Alkyl amines are stronger bases than ammonia because the alkyl groups are electron donors and increase the electron density on nitrogen. Aromatic amines, on the other hand, are weaker bases than ammonia. Delocalization of the unshared pair of electrons on nitrogen onto the aromatic ring means the electrons are not available to be shared with acidic protons. Furthermore, the Sandmeyer reaction is a versatile means of replacing the amine group with number of substituents. Herein, a diazonium salt (9) can be formed by the reaction of nitrous acid with an amine in acid solution through the formation of a nitroso ion as an intermediate. R is alkyl or aryl.

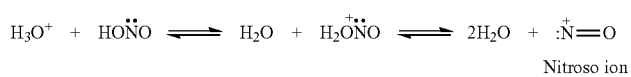

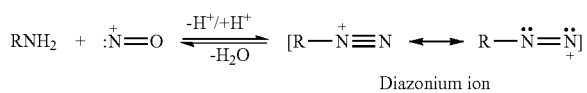

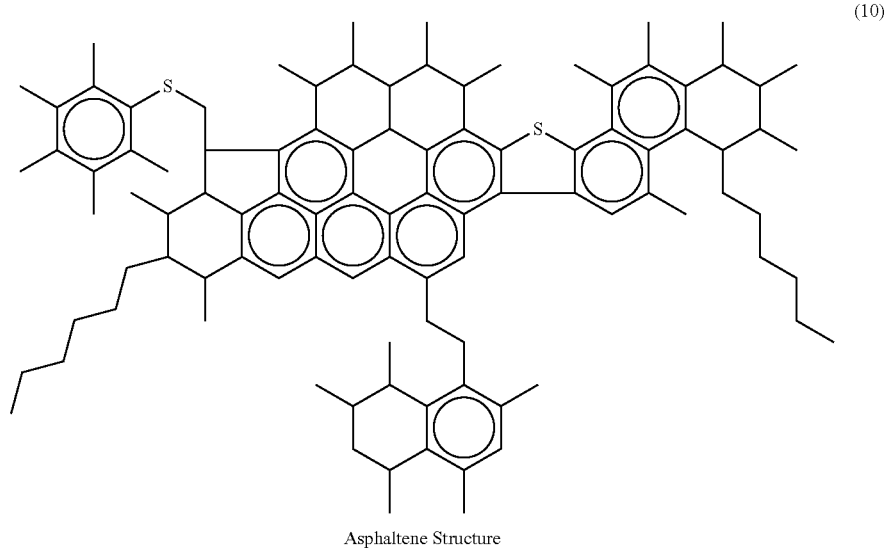

Asphaltene Structure

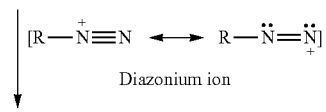

-continued

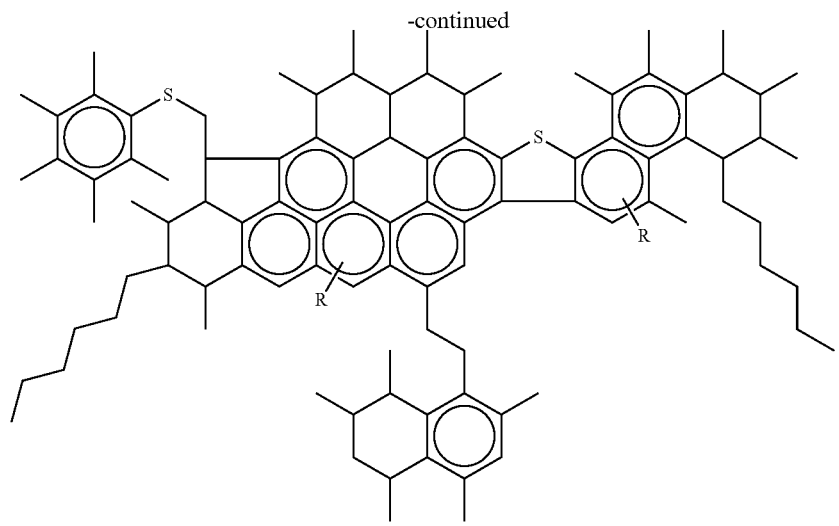

The chemical reaction results in the proposed asphaltene structure after reacting with amines (10). In the structure, R is indicative of an aryl or alkyl group which has been substituted onto the polycyclic core of the asphaltene.

The aforementioned Sandmeyer reaction allows substitution of an alkyl group or aryl group to the asphaltene (10) at any of the initial Hydrogen positions on the unreacted asphaltene structure as shown in the location indicated in the chemical structure. Alkyl and/or aryl additions to at least one dibenzothiophene group, as well as an alkyl or aryl addition to at least one benzoanthracene group results in the formation of a functionalized asphaltene. Further alkyl or aryl substitutions may occur at the cyclopentylmethyl 2,3,4,5,6-pentamethylphenyl sulfane (3) or the 1,2,4,5,7-pentamethyl-8-propyl-1,2,3,4-tetrahydronaphthalene (4) groups to further functionalize the asphaltene.

Therefore the alkyl or aryl addition to the asphaltene will result in either additional long aliphatic chains or in increasing the cyclic core. Either of these additions results in the formation of a functionalized asphaltene. Furthermore, these additions may increase the flocculation properties of the reacted asphaltenes, and therefore, render them easier to remove from the petroleum feed stream, or alternatively these groups may further solubilize the asphaltenes and maintain them in the petroleum feed stream.

The experimentation into the reactivity of asphaltenes with primary, secondary and tertiary amines includes, but is not limited to the following amines:

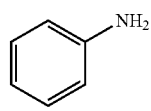

(11)

aniline (11) is a primary aromatic amine

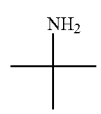

(12)

t-butylamine (12) is a primary amine

-continued

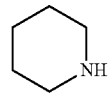

(13)

piperidine (13) is a cyclic secondary amine

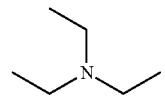

(14)

triethylamine (14) is a tertiary amine

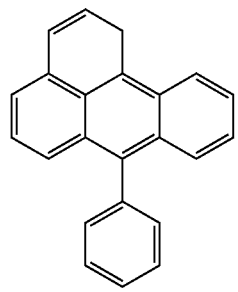

(15)

For example, the reaction of aniline with 1H-benzo[de]anthracene of the asphaltene polycyclic core forms the 7-phenyl-1H-benzo[de]anthracene compound as shown (15), and the reaction of aniline with 2-methyldibenzo[b,d]thiophene yields 2-phenyldibenzo[b,d]thiophene (16).

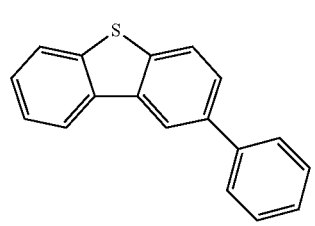

(16)

Furthermore to the alkyl and aryl substitutions, the substitution of polar substituents onto the aromatic rings of the asphaltenes raises the solubility parameters of the asphaltenes rendering them less soluble in the balance of the petroleum resid and heavy oil, which is non-polar or less polar by comparison, thereby resulting in the selective precipitation of the polar group functionalized asphaltene from the heavy hydrocarbon feed stream.

A second aspect of the present invention is directed toward the reaction of asphaltenes from Saudi crude oil residues that have undergone electrophilic aromatic substitution through the formation of a nitronium ion leading to a nitrated asphaltene. The nitronium ion, is a generally reactive cation created by the removal of an electron from the paramagnetic nitrogen dioxide molecule or from the protonation of nitric acid.

Herein, the reaction mechanism for the generation of electrophile $NO_2^+$ and product formation after reacting with various asphaltenes is disclosed. The nitration of asphaltenes obtained from the four Saudi crude oil sources resulted in the formation of nitrated products.

The aromatic ring systems of asphaltenes undergo nitration with concentrated $HNO_3$ in the presence of concentrated $H_2SO_4$, along with a Lewis acid catalyst. The Lewis acid helps in the generation of electrophile $NO_2^+$ called nitronium ion. This electrophile, nitronium ion, attacks the $\pi$ electrons of aromatic ring system of asphaltenes to yield a resonance stabilized carbocation intermediate called a benzenonium ion. A hydrogen ion is removed rapidly from the intermediate to yield a substituted product. The hydrogen ion, $H^+$, combines with $HSO_4^-$ to regenerate the catalyst, $H_2SO_4$. IR spectroscopy confirms the nitration of all asphaltenes. A proposed reaction mechanism for the generation of electrophile $NO_2^+$ (17) and product formation after reacting with various asphaltenes (18) is shown. The reactions indicate the formation of the desired nitrated asphaltenes. Although the present disclosure is directed to the use of the electrophile ($NO_2^+$) nitronium ion, the use of other nitrating agents is included in the scope of the invention. These nitrating agents, given as $NO_2Y^+$, can include, but are not limited to, tetrafluoroborate, nitrito onium salts, dimethylnitrosulfonium ion, nitryl chloride, chloropicrin, and tetranitromethane.

(17)

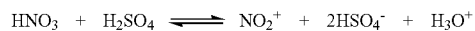

Nitronium ion (18)

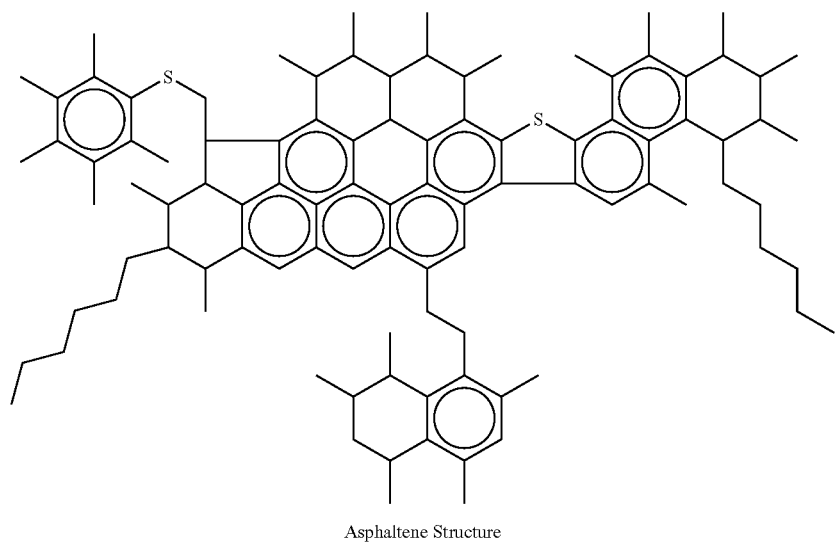

Asphaltene Structure $\downarrow NO_2^+$

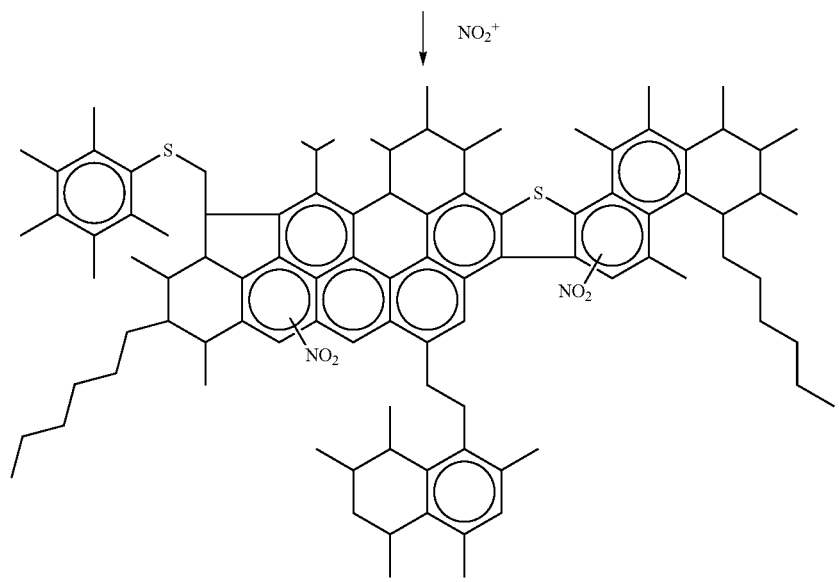

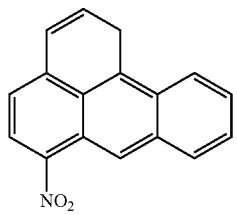

(19)

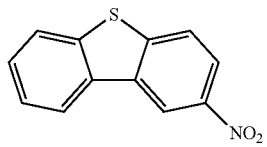

(20)

For example, as a result of the nitration, the reaction between the 1H-benzo[de]anthracene of the asphaltene polycyclic core forms 6-nitro-1H-benzo[de]anthracene (19) and the nitration reaction with 2-methyldibenzo[b,d]thiophene yields 2-nitrodibenzo[b,d]thiophene (20).

Furthermore, the nitration of at least one dibenzothiophene group, as well as the nitration of at least one benzoanthracene group results in the formation of a functionalized asphaltene. Further nitration may occur at the cyclopentylmethyl 2,3,4,5,6-pentamethylphenyl sulfane (3) or the 1,2,4,5,7-pentamethyl-8-propyl-1,2,3,4-tetrahydronaphthalene (4) groups to further functionalize the asphaltene.

Previous characterization of the structure of Saudi crude asphaltenes by x-ray diffraction Nuclear Magnetic Resonance (NMR), and HP-GPC is incorporated herein by reference in its entirety [Shirokoff, John W., Siddiqui, Mohammad N., Ali, Mohammad F., Characterization of the Structure of Saudi Crude Asphaltenes by X-ray Diffraction, *Energy & Fuels* 1997, 11, 561-565].

The use of $^{13}$C NMR in the analysis of a mixture of petroleum-based hydrocarbons is well known. Carbon-13 NMR has a large range of chemical shifts (0-250 ppm), which offers an excellent opportunity for chemical shift characterization of different carbons. For a simple hydrocarbon system, the range for aliphatic carbons is approximately 0-50 ppm. Additively rules can be used to estimate chemical shifts for a carbon in a given molecular structure. Additionally, there are well-established and extensive tables correlating chemical shifts with molecular structures. The recognized use of these techniques, and the prior characterization of Saudi crude asphaltenes, allows one familiar with the art to quantitatively estimate the reactivity of asphaltenes at the molecular level with both the nitrating and amine-directed addition of alkyl- and/or aryl-groups.

Studies of electrophilic aromatic substitution reactions on polycyclic aromatic and polycyclic heteroaromatics, both in model compounds and with resids, have demonstrated selectivity for attacking the more electron rich polycyclic aromatics and heteroaromatics. Decreasing or increasing the number of fused polycyclic rings, and/or heteroatom content and/or increasing the extent of alkyl substitution will affect the solubility of the Saudi crude asphaltenes. This, in turn, has important commercial implications for the petroleum industry in assessing the removal, or solubilization, of asphaltenes.

Such electrophilic aromatic substitution processes as disclosed herein utilize little, if any, solvent, and the substitution process is more sensitive in its selectiveness. This selectiveness results in a decreased precipitation of non-asphaltic molecules, and moreover, there is also a lowered amount of residual asphaltene molecules in the de-asphalted oil fraction.

IR spectrometry is able to distinguish between chemical compounds by detecting the selective absorption of different IR wavelengths by chemical bonds; thus for every IR-active compound present in a sample, there is a unique IR spectral signature which enables its identification. Using this technique, it is now possible to ascertain the addition of alkyl or aryl groups onto the polycyclic core structure of the asphaltene, rendering it a functionalized asphaltene. Tables A and B give absorption frequencies of some functional groups observed in IR spectrophotometry in crude asphaltenes and assignment of $^1$H and $^{13}$C NMR spectra, respectfully.

TABLE A

Absorption Frequencies of Some Functional Groups Observed in IR Spectroscopy in Crude Asphaltenes

| Functional Groups | Frequencies, $\nu$ (cm$^{-1}$) | Peak Intensity |
|---|---|---|
| —OH | 3100-3500 | Broad |
| —NH pyrrolic | 3480 | Weak |
| —CH | 2970 | Very strong |
|  | 2850 | Very strong |
| —CO=O dimer | 2715 | Weak |
| —C=C aromatic | 1590 | Strong |
| —C=N | 1450 | Strong |
| —C—N | 1370 | Strong |
| —C—O | 1045 | Weak |

TABLE B

| Type | Chemical Shift (ppm) | Assignment |
|---|---|---|
| Assignment of $^1$H NMR Spectra | | |
| Aliphatic | 0.5-4.0 H$_{sat.}$ | Aliphatic protons |
|  | 1.9-4.0 H$_\alpha$ | Protons in α-position in paraffinic carbon chain with respect to an aromatic ring |
|  | 1.6-1.9 H$_n$ | Naphthenic protons |
|  | 1.0-1.6 H$_\beta$ | Protons at β-position |
|  | 1.0-1.9 Total H$_\beta$ | |
|  | 0.5-1.0 H$_\gamma$ | Protons at γ, or further removed in paraffinic carbon chain |
| Aromatic | 6.0-9.0 H$_{ar}$ | Aromatic protons |
| Assignment of $^{13}$C NMR Spectra | | |
| Type | Chemical Shift (ppm) | Assignment |
| Aliphatic | 0-70 C$_{sat}$ | Aliphatic carbons |
| Aromatics | 110-160 C$_{ar}$ | Aromatic carbons |

The examples below are intended to further illustrate protocols for preparing and characterizing the various embodiments of high density polyethylene described herein, and are not intended to limit the scope of the claims.

Example 1

Sample Collection

The following four varieties of marketable crude oils produced by the Saudi Arabian Oil Company (Saudi Aramco)

were procured from Ras Tanura refinery, Saudi Arabia and were analyzed in this study: Arabian Extra Light (AB), Arabian Light (AL), Arabian Medium (AM) and Arabian Heavy (AH).

Arabian Extra Light comes from the Berri, Saudi Arabia field and is produced from the upper Jurassic age Arab zone reservoirs, generally oolitic and dolomitic limestone.

Arabian Light is produced from the Ghawar field, which is the largest onshore oil field in the world, and it is also derived from the upper Jurassic age Arab zone reservoirs.

Arabian Medium is produced from the Jurassic age Arab zone reservoirs as multi-stage separated oil from a blend of the following fields: 65% Khursaniya, 25% Qatif, and 10% Abu-Safah.

Arabian Heavy is comprised of crude oil from an offshore field, Safaniya, located about 125 miles northwest of the exporting terminal Ras Tanura and known to be the world's largest offshore oil field. Safaniya oil is produced from the lower Cretaceous age Arab zone reservoirs.

Herein Arabian Extra Light will be referred to as AB; Arabian Light will be referred to as AL; Arabian Medium will be referred to as AM; and Arabian Heavy will be referred to as AH.

Separation of Asphaltenes

First, 7.0 g of heavy residue was transferred to a 200-ml beaker and heated with a very small amount of n-heptane in order to homogenize the solution. This residue solution, when well mixed, was transferred to a 2-L flask and 700 ml of n-heptane was added to the same flask. The flask containing the residue solution was fitted with a mechanical stirrer and placed on the water bath. The residue solution was heated at 90° C. on the steam bath with continuous stirring for approximately 2 hours in order to maximize the solubility of residue in n-heptane. After two hours of mixing, the residue solution was covered with aluminum foil and was left on the working bench to cool at room temperature for approximately 24 hours. The long cooling time produces a more efficient precipitation of asphaltenes. The residue solution was filtered using a Millipore filtration apparatus with 0.8 μm pore size filter paper. All insoluble material was Soxhlet extracted with toluene and filtered again using the same filtering apparatus. The insoluble material was removed as sludge (coke), and the soluble material, including asphaltenes, was recovered after completely evaporating toluene. The asphaltenes were collected in a 250-ml beaker and washed several times with small portions of n-heptane, in order to remove any traces of maltenes, until washings became colorless. The recovered asphaltenes were dried in an oven for approximately 2 hours at 105° C. to obtain a constant weight. The filtrate, maltenes, were recovered by evaporating the n-heptane on the steam bath using a rotavapor with continuous blowing of dry nitrogen until a constant weight of maltenes was obtained.

Nitration of Asphaltene

In a test tube, 2.0 ml of concentrated $H_2SO_4$ was cooled to 0° C. and, subsequently, the addition of a brown-colored solution comprising 0.1 g of asphaltene in 4.0 ml of sulfolane was made. This mixture was cooled to 0-10° C. Now 2.0 ml of concentrated $HNO_3$ and 2.0 ml of concentrated $H_2SO_4$ acid were placed in a 50.0 ml Erlenmeyer flask and cooled in an ice bath. After a few moments, the cooled acid mixture from the Erlenmeyer flask was transferred drop-wise, using a Pasteur pipette, into the cooled asphaltene solution while maintaining constant swirling. During the addition, the reaction mixture temperature was maintained in the range of 5 to 15° C. When all the acid mixture was added, the solution was warmed to room temperature. After 15 minutes, the warmed solution was poured onto 10.0 g of cracked ice in a small beaker with continuous stirring. The solid product was isolated by suction filtration using a small Buchner funnel and washed well with water followed by 2×10.0 ml portion of ice-cold methanol. The crude product afforded nitrated asphaltene.

Reaction of Amines with Asphaltene

In 100-ml Erlenmeyer flask, 3.0 g amine (aniline, piperidine, t-butyl amine and triethyl amine), was initially placed in 10.0 ml distilled water. Subsequently 6.0 ml concentrated HCl was added and this solution was warmed slowly on a hot plate to make it homogeneous. The mixture was then cooled to room temperature in an ice-bath while bubbling $N_2$ gas to displace the air. When the amine solution was in the range of 0-5° C., a solution of 1.8 g $NaNO_2$ in 6 ml of distilled water was added slowly to the cooled amine solution. After 5 minutes, 0.5 g of asphaltene (Arab heavy, medium, light and extra light) in 5.0 ml of sulfolane was added to the Erlenmeyer flask containing the amine solution. The mixture was allowed to stand without cooling for 5 minutes under $N_2$ gas and then warmed to 40° C. At this point, a vigorous reaction took place; the mixture was then heated on a steam bath for 30 minutes. The solution was cooled in ice, kept over-night and filtered using Buchner funnel. Residue product was washed with water, dried and collected for analysis.

Analysis

FIG. 1 shows an overlaid IR spectrum of AH asphaltene after reacting with different amines.

IR Spectra Analysis of Aniline and AH Asphaltene Reacted Product

The prominent peaks observed in the AH asphaltene spectrum are:

Broad and weak at 3337 may be due to some overtones;

Sharp and strong at 2922, 2852 are may be due to aromatic or alkene C—H stretching;

Sharp and medium peak at 1594 may be due to C—C stretch in ring;

Sharp and medium peak at 1458 may be due to C=C stretch;

Sharp and small peak at 1375 may be due to asymmetrical $CH_3$ vibrations.

The following extra peaks were observed after the reaction of aniline with AH asphaltene:

Sharp and medium peak at 1495 may be due to aromatic C—C stretching; Weak and broad peak at 1234 may be due to C—N stretching for primary amines; Medium and sharp peaks as doublet at 752, 693 may be due to aromatic stretching.

IR Spectra Analysis of Piperidine and AH Asphaltene Reacted Product

Peaks at 2922 and 2852 which are sharp and strong represent AH and they may be due to $CH_2$ asymmetrical and symmetrical stretching.

A weak and broad peak at 3024 represents aromatic or alkene C—H stretch, which is absent in the AH spectrum.

Broad and weak peaks at 1601 may be due to C=C stretch and sharp and medium peaks at 1458 are also due to C=C stretch; it is also present in the AH spectrum.

Sharp and weak peaks at 1375 may be due to $CH_3$ vibrations; it is also present in the AH spectrum.

IR Spectra Analysis of t-Butylamine and AH Asphaltene Reacted Product

In this spectrum many peaks that represent aromatic characters were observed.

Broad and strong peaks exist at 2923 and 2854; which are also present in AH. These may be due to $CH_2$ asymmetrical and symmetrical stretching;

A sharp and weak peak at 2731 is due to a carbonyl group overtone peak, and a carbonyl character peak is present at 1732 which is weak and sharp.

Peaks at 1940, 1856 and 1800 are overtones peaks;

Sharp and strong peaks at 1602, 1493 and 1458 are due to C=C stretching;

Sharp and medium peaks at 1080 and 1031 represent aromatic inplane bending;

Sharp and strong doublet at 729 and 694 represents C—H aromatic bending.

IR Spectra Analysis of Triethylamine and AH Asphaltene Reacted Product

Strong and sharp peaks at 2923 and 2853 represent the AH asphaltene spectrum. The other peaks which represents AH are at 1602, 1493, 1376 and 1031.

The sharp peaks and medium peaks at 728 and 693 represent C—H rocking of alkanes of triethylamine.

FIG. 2 shows an overlaid IR spectrum of AM asphaltene after reacting with different amines.

IR Spectra Analysis of Aniline and AM Asphaltene Reacted Product

The prominent peaks observed in the AM asphaltene spectrum are:

Sharp and strong at 2922, 2851 may be due to aromatic or alkene C—H stretching;

Sharp and medium peak at 1594 may be due to C—C stretch in ring;

Sharp and medium peak at 1460 may be due to C=C stretch;

Sharp and small peak at 1375 may be due to asymmetrical $CH_3$ vibrations.

The extra peaks may be due to presence of aniline, these peaks are:

Broad and weak peaks at 3749, 3307, and 3044 may be due to N—H asymmetrical stretching;

Weak and sharp peak at 1235 may be due to C—N stretching for primary amines; Medium and sharp peaks as doublet at 752, 693 may be due to aromatic stretching.

IR Spectra Analysis of Piperidine and AM Asphaltene Reacted Product

Peaks at 2922 and 2851 represent AM and they may be due to $CH_2$ asymmetrical and symmetrical stretching.

A weak and broad peak is observed at 1727; it may be due to some carbonyl characters.

Broad and weak peak at 1599 and sharp and medium peak at 1458 may be due to C=C stretch; it is also present in AH spectrum.

Sharp and weak peak at 1376 may be due to $CH_3$ vibrations; it is also present in AM spectrum.

A small and broad peak is observed at 1122 it may be due to C—N stretch.

IR Spectra Analysis of t-Butylamine and AM Asphaltene Reacted Product

Peaks at 2921 and 2851 represent AM and they may be due to $CH_2$ asymmetrical and symmetrical stretching.

Broad and weak peak at 1601 and sharp and medium peak at 1458 may be due to C=C.

Sharp and medium peak at 1376 may be due to $CH_3$ vibrations; it is also present in AM spectrum.

Weak and broad peaks at 1030 and weak and sharp peak at 728 represent aromatic character peaks which are not present in AM spectrum.

IR Spectra Analysis of Triethylamine and AM Asphaltene Reacted Product

The prominent peaks observed in the AM asphaltene spectrum are:

Sharp and strong at 2922, 2851 which may be due to aromatic or alkene C—H stretching;

Sharp and medium peak at 1601 may be due to C—C stretch in ring;

Sharp and medium peak at 1458 may be due to C=C stretch;

Sharp and small peak at 1376 may be due to asymmetrical $CH_3$ vibrations;

Weak peaks at 1031 and 813 due to AM.

The following peaks represent triethylamine:

Broad and weak peak at 1274 may be due to C—N stretching;

Sharp and weak peaks at 728 and 694 may be due to C—H stretching.

FIG. 3 shows an overlaid IR spectrum of AL asphaltene after reacting with different amines.

IR Spectra Analysis of Aniline and AL Asphaltene Reacted Product

The prominent peaks observed in the AL asphaltene spectrum are:

Broad and weak at 3270 may be due to some overtones;

Sharp and strong at 2919, 2851 may be due to aromatic or alkene C—H stretching;

Sharp and medium peak at 1595 may be due to C—C stretch in ring;

Sharp and medium peak at 1465 may be due to C=C stretch;

Sharp and small peak at 1375 may be due to asymmetrical $CH_3$ vibration;

Weak and sharp peak at 1027 may be due to aromatic inplane bending;

Peaks at 865, 812 and 729 may be due to aromatic characters.

The extra peaks may be due to presence of aniline, these peaks are:

Strong and broad peak at 1234 which may be due to C—N stretching for primary amines;

Medium and sharp peaks as doublet at 729, 693 which may be due to aromatic stretching.

IR Spectra Analysis of Piperidine and AL Asphaltene Reacted Product

In this spectrum due to the presence of piperidine the intensities of all the peaks are decreased.

Peaks at 2920, 2850, 1601, and 1458 are from AL, but with decrease in intensities.

There are also weak peaks at 1375, 693 and 728 which are extra peaks and these show aromatic character in the spectrum.

IR Spectra Analysis of t-Butylamine and AL Asphaltene Reacted Product

Peaks at 2921 and 2850 represent AL which are due to $CH_2$ asymmetrical and symmetrical stretching.

Weak and broad peak at 3024 represents aromatic or alkene C—H stretch.

Peaks at 1602, 1494 and 1458 are due to C=C stretch.

Sharp and medium peak at 1375 may be due to $CH_3$ vibrations.

Peaks at 1031, 728 and 694 represent aromatic characters which are not present in AL spectrum.

IR Spectra Analysis of Triethylamine and AL Asphaltene Reacted Product

In this spectrum sharp and strong peaks at 2921 and 2851 represents AL; these may be due aromatic or alkene characters of AL.

The other common peaks of AL present in this spectrum are at 1457, which may be due to C=C stretch, 1036 and at 859.

Sharp and weak peak at 694; and sharp and medium peak at 728 which represent C—H rocking of alkane groups present in triethylamine.

FIG. 4 shows an overlaid IR spectrum of AB asphaltenes after reacting with different amines.

IR Spectra Analysis of Aniline and AB Asphaltene Reacted Product

The prominent peaks observed in the AB asphaltene spectrum are:

Broad and weak at 3375 may be due to some overtones;

Sharp and strong at 2916, 2848 may be due to aromatic or alkene C—H stretching;

Sharp and medium peak at 1596 may be due to C—C stretch in ring;

Sharp and medium peak at 1462 may be due to C=C stretch;

Sharp and small peak at 1376 may be due to asymmetrical $CH_3$ vibrations.

The extra peaks may be due to presence of aniline; these peaks are:

Sharp and medium peak at 1724 which may be due to some carbonyl characters group;

Medium and broad peak at 1270 may be due to C—N stretching for primary amines;

Weak and medium peak at 1125 may be due to C—H wagging;

Medium and sharp peak at 1072 may be due to C—N stretching;

Medium and sharp peaks as doublet at 752, 693 may be due to aromatic stretching.

IR Spectra Analysis of Piperidine and AB Asphaltene Reacted Product

The common peaks of AB are at 2921, 2848 and 1376.

The other peaks which are present in this spectrum due to the presence of piperidine are:

Sharp and medium peak at 3027 which may be due to aromatic or alkenes C—H stretch;

Peaks at 1602, 1494 and 1460 which represent aromatic character and are due to C=C stretch.

Peaks at 1031, 728 & 694 which also represent aromatic characters which are absent in the AB spectrum.

IR Spectra Analysis of t-Butylamine and AB Asphaltene Reacted Product

In this spectrum, peaks are present at 2917 and 2848 which represent AB, and are due to $CH_2$ asymmetrical and symmetrical stretching.

Medium peaks at 1603 and 1461 represent C=C stretching;

Sharp and weak peaks at 1374 represent asymmetrical $CH_3$ vibrations;

Weak and broad peaks at 1029 represent aromatic inplane bending;

Sharp and medium doublet at 729 and 694 represent C—H aromatic bending.

IR Spectra Analysis of Triethylamine and AB Asphaltene Reacted Product

In this spectrum, the strong and sharp peaks at 2916, 2848, 1461, and 1376 represents AB.

The following peaks represent triethylamine:

Broad and weak peak at 1273 due to C—N stretching;

Broad and weak peak at 1124 may be due to C—N stretch of aliphatic amines;

Peak at 727 may be due to C—H rocking of alkanes.

NMR Spectroscopy of Reactions of Amines with Asphaltenes

Aniline/AH

A weak intensity peak at 1.2520 is due to an aliphatic hydrocarbon of AH, and low intensity peaks at 7.44 and 7.236 may be due to aromatic AH. There is also a small significant peak at 6.8752 due to aniline.

FIG. 5 shows the proton NMR spectrum of AH asphaltene after reacting with aniline.

Table 1 indicates the percentage and type of hydrocarbons present in AH asphaltenes.

TABLE 1

| Type of hydrocarbons | Percentage |
| --- | --- |
| Aliphatic | 78.45% |
| Aromatic | 21.55% |

Aniline/AM

A plurality of peaks at 0.8664 and 0.8786 with low intensity represent aliphatic AM, and there are several peaks with many multiplicities in an aromatic region from which the strongest peak at 7.248 corresponds to AM. The peak at 6.8655 corresponds to aromatic aniline.

Table 2 indicates the percentage and type of hydrocarbons present in AM asphaltenes.

TABLE 2

| Type of hydrocarbons | Percentage |
| --- | --- |
| Aliphatic | 77.92% |
| Aromatic | 22.07% |

Aniline/AL

There is a strong peak at 1.4253 and there are several peaks with multiplets at 7.49 and 7.3390 which may be due to the presence of aniline.

There are peaks at 7.2267 and 1.2520 which may represent AL, but these peaks are of lower intensity when compared to the pure AL spectra.

Table 3 indicates the percentage and type of hydrocarbons present in AL asphaltenes.

TABLE 3

| Type of hydrocarbons | Percentage |
| --- | --- |
| Aliphatic | 79.46% |
| Aromatic | 20.53% |

Aniline/AB

A very strong peak is observed at 1.2545 due to aliphatic AB, and several peaks were observed with multiplicity in the region of 6.82 to 7.465 due to aromatic aniline and AB.

Table 4 indicates the percentage and type of hydrocarbons present in AH asphaltenes.

TABLE 4

| Type of hydrocarbons | Percentage |
| --- | --- |
| Aliphatic | 76.12% |
| Aromatic | 37.87% |

Piperidine/AH

In this spectrum all the peaks represents AH only. Characteristics peaks of piperidine are absent. Table 5 indicates the percentage and type of hydrocarbons present in AH asphaltenes.

TABLE 5

| Type of hydrocarbons | Percentage |
| --- | --- |
| Aliphatic | 99.16% |
| Aromatic | 0.83% |

Piperidine/AM

In this spectrum also it is observed that all the peaks which represent only AM are present, but with low intensity, compared to original AM spectra. Table 6 indicates the percentage and type of hydrocarbons present in AM asphaltenes.

TABLE 6

| Type of hydrocarbons | Percentage |
| --- | --- |
| Aliphatic | 90.78% |
| Aromatic | 9.21% |

Piperidine/AL

In this spectrum there is a weak peak at 1.6279 which may be due to presence of piperidine.

There are peaks at 7.2462, 1.2520 and 0.8762 which are due to AL, but these peaks are with less intensity as compared to the pure AL spectra. Table 7 indicates the percentage and type of hydrocarbons present in AL asphaltenes.

TABLE 7

| Type of hydrocarbons | Percentage |
| --- | --- |
| Aliphatic | 88.53% |
| Aromatic | 11.46% |

Piperidine/AB

FIG. 6 shows the proton NMR spectrum of AB asphaltene after reacting with piperidine.

A very strong peak at 1.2520 is due to aliphatic AB and another peak at 7.2511 is due to the aromatic character of AB. In this spectrum, the peaks which represent piperidine are not present. Table 8 indicates the percentage and type of hydrocarbons present in AB asphaltenes.

TABLE 8

| Type of hydrocarbons | Percentage |
| --- | --- |
| Aliphatic | 90.79% |
| Aromatic | 9.20% | t-Butylamine/AH

In this NMR spectrum, only one significant peak was observed with strong intensity at 1.4253, with a singlet. Also, a very low intensity peak at 7.2413 was observed, which is due to AH. Table 9 indicates the percentage and type of hydrocarbons present in AH asphaltenes.

TABLE 9

| Type of hydrocarbons | Percentage |
| --- | --- |
| Aliphatic | 99.40% |
| Aromatic | 0.59% | t-Butylamine/AM

In this spectrum only two significant peaks were observed; one in an aromatic region at 7.2340 and one in an aliphatic region at 1.2520. These two peaks represent AM only and no other significant peaks are observed in this spectrum. Table 10 indicates the percentage and type of hydrocarbons present in AM asphaltenes.

TABLE 10

| Type of hydrocarbons | Percentage |
| --- | --- |
| Aliphatic | 92.11% |
| Aromatic | 7.88% | t-Butylamine/AL

In this spectra also, the only peaks present are due to AL. The peaks are at 7.2413 and 1.2545.

Table 11 indicates the percentage and type of hydrocarbons present in AM asphaltenes.

TABLE 11

| Type of hydrocarbons | Percentage |
| --- | --- |
| Aliphatic | 90.64% |
| Aromatic | 9.36% | t-Butylamine/AB

FIG. 7 shows the proton NMR spectra of AB asphaltenes after reacting with t-butylamine.

In this spectrum significant peaks of AB at 7.2120 and 1.2569 were observed, and no other peaks were observed. Table 12 indicates the percentage and type of hydrocarbons present in AB asphaltenes.

TABLE 12

| Type of hydrocarbons | Percentage |
| --- | --- |
| Aliphatic | 88.88% |
| Aromatic | 11.11% |

Triethylamine/AH

In this spectrum, peaks which represent AH are present. An extra peak at 1.4278 is also present which does not represent AH or triethylamine. Table 13 indicates the percentage and type of hydrocarbons present in AM asphaltenes.

TABLE 13

| Type of hydrocarbons | Percentage |
| --- | --- |
| Aliphatic | 95.34% |
| Aromatic | 4.66% |

Triethylamine/AM

In this spectrum, peaks which represent AM are present, and no other significant peaks are present. Table 14 indicates the percentage and type of hydrocarbons present in AM asphaltenes.

TABLE 14

| Type of hydrocarbons | Percentage |
| --- | --- |
| Aliphatic | 91.73% |
| Aromatic | 7.57% |

Triethylamine/AL

FIG. 8 shows the proton NMR spectra of AL asphaltenes after reacting with triethylamine.

In this spectrum, peaks which represent AL are present, but the intensity of the aromatic peak is very low. Table 15 indicates the percentage and type of hydrocarbons present in AL asphaltenes.

TABLE 15

| Type of hydrocarbons | Percentage |
|---|---|
| Aliphatic | 98.88% |
| Aromatic | 1.11% |

Triethylamine/AB

In this spectrum, only the peaks which represent AB are present; one in an aromatic region at 7.2511 and the other in an aliphatic region at 1.2520. Table 16 indicates the percentage and type of hydrocarbons present in AB asphaltenes.

TABLE 16

| Type of hydrocarbons | Percentage |
|---|---|
| Aliphatic | 87.48% |
| Aromatic | 12.51% |

$^{13}$CNMR Spectra Interpretations

Aniline

AH: In this spectrum, all the peaks of AH asphaltenes are present but there are additional peaks which represent aniline at 129.5778, 115.3639 and at 118.6953.

AM: In this spectrum also, the prominent peaks at 77.2712, 77.0162 and 76.7612 of AM are present with these peaks small significant peaks at 115.3804, 120.4802 and at 129.7094 which represents aniline AL: In this spectrum peaks which are significant to AL and aniline are present. Peaks of aniline are at 155.94, 118, 115, and at 129.

AB: In this spectrum all the peaks which represent AB are present at 77.2712, 77.0162 and 76.7612, and there are also prominent peaks of aniline, for example: peaks at 155.7763, and a plurality of peaks at 118 and 115. These peaks are attributed to the presence of aniline.

FIG. 9 shows the carbon NMR spectra of AB asphaltenes after reacting with aniline.

t-Butylamine

AH: All the peaks represent AH only, but due to the presence of t-butylamine the intensities of these peaks are reduced.

AB: In this spectrum all the peaks which represent AB are present. There is a very small peak at 1562.38 which represents t-butylamine, but other prominent peaks of t-butylamine are absent.

AL: In this spectrum also there are no prominent carbon peaks of t-butylamine all the peaks represents AL only.

AM: All the peaks represent in IR are from AM asphaltene only, no significant peaks of t-butylamine were observed indicating almost no reaction.

FIG. 10 shows the carbon NMR spectra of AL asphaltenes after reacting with butylamine.

Piperidine

AH: This spectrum indicates there is no significance of addition of piperidine to AH. In this spectrum all the peaks represents AH only, so no significant peaks of piperidine are observed.

FIG. 11 shows the carbon NMR spectra of AH asphaltenes after reacting with piperidine.

AM: In this spectrum all the prominent peaks of AM are present but there are some extra peaks at 79.3276, and 59.5780 which may be due to presence of piperidine.

AL: In this spectrum all the peaks which represent AL are present but the presence of piperidine does not have any effect, and no significant peaks of piperidine were observed.

AB: All the peaks which represent AB are present in this spectrum but there is a very small intense peak at 44.5087 which represents piperidine.

Triethylamine

AH: In this spectrum all the peaks which represent AH are present, but there are also peaks at 53.3101 and 22.7191 which represent triethylamine.

AL: In this spectrum no extra peaks of triethylamine are observed, but due to the presence of triethylamine, the intensities of the significant peaks characteristic of AL are decreased.

AB: There are peaks in this spectrum which represents AB and there are some extra peaks 37.1139 to 14.1316 which may be due to presence of triethylamine.

AM: The following peaks represent triethylamine: Broad and weak peak at 1274 may be due to C—N stretching and sharp and weak peaks at 728 and 694 may be due to C—H stretching.

FIG. 12 shows the carbon NMR spectra of AB asphaltenes after reacting with triethylamine.

Nitration Spectra Analysis

Nitrated AH IR Spectra

Due to the presence of nitro group in AH all the peaks are strong and broad

Strong and broad peaks at 2839, 3297 and 2921 represents AH

Strong and broad peaks at 1699, 1542 and 1029 are due to nitration.

FIG. 13 shows the IR spectra of AH asphaltenes after nitration.

Nitrated AM IR Spectra

In this spectrum only one prominent peak of AM is present i.e. at 2924.

The other peaks are due to the presence of nitro groups:

Broad and weak peak at 1653 may be due to asymmetrical stretching of $NO_2$;

A peak at 1540 maybe due to asymmetrical aromatic $NO_2$ stretching;

Strong and broad peaks at 1344 and 1227 may be due to symmetrical aromatic $NO_2$ group.

Weak and broad peak at 850 may be due to N—O stretching.

FIG. 14 shows the IR spectra of AM asphaltenes after nitration.

Nitrated AL IR Spectra

In this spectrum, the peaks at 3421, 2921 and 2850 are due to AL.

A peak at 1647 represents N=O stretch;

A peak at 1535 may be due to aromatic $NO_2$ stretching;

Strong and broad peak at 1343 may be due to symmetrical $NO_2$ group;

FIG. 15 shows the IR spectra of AL asphaltenes after nitration.

Nitrated AB IR Spectra

Due to presence of nitro groups, the intensities of prominent AB peaks are reduced.

The peaks at 2915 and 2839 may be due to AB. The peaks at 1594, 1453 and 1373 represent AB, but the intensities are reduced.

In this spectrum the prominent peaks of nitro groups at 850, 1540 1227 are absent.

FIG. 16 shows the IR spectra of AP asphaltenes after nitration.

NMR Spectroscopy of Nitration

Nitration of AH

In this spectrum there in no shift in the aromatic region i.e. the aromatic peak at 7.2365 is the same in both the original AH spectrum and in the nitration spectrum, but there are shifts in the aliphatic region from 1.2527 to 1.4278, and a peak at 2.1722 is also present in nitration. Table 17 indicates the percentage and type of hydrocarbons present in AH asphaltenes.

TABLE 17

| Type of hydrocarbons | Percentage |
| --- | --- |
| Aliphatic | 98.44% |
| Aromatic | 1.55% |

Nitration of AM

In the nitration of AM, a prominent peak of nitration in the aliphatic region at 1.4253 is observed, and a decrease in intensity of an aromatic peak at 7.24 is also observed, when compared to the original AM spectra. Table 18 indicates the percentage and type of hydrocarbons present in AM asphaltenes.

TABLE 18

| Type of hydrocarbons | Percentage |
| --- | --- |
| Aliphatic | 97.24% |
| Aromatic | 2.75% |

Nitration of AL

Due to the nitration of AL, the shifting of aromatic and aliphatic peaks with a notable decrease in their intensities had been observed. The aromatic peak of AL shifted from 7.2548 to 6.2700 with a decrease in intensity, and the prominent aliphatic peak of AL shifted from 1.2520 to 1.4278, with a notable decrease in intensity as well.

FIG. 17 shows the proton NMR spectra of AL asphaltenes after nitration.

Table 19 indicates the percentage and type of hydrocarbons present in AL asphaltenes.

TABLE 19

| Type of hydrocarbons | Percentage |
| --- | --- |
| Aliphatic | 99.82% |
| Aromatic | 0.20% |

Nitration of AB

In this spectrum, only one change is observed in that there is an increase in intensity of peaks in the known aromatic and aliphatic region i.e. at 1.2545 and 7.2.

FIG. 18 shows the proton NMR spectra of AB asphaltenes after nitration.

Table 20 indicates the percentage and type of hydrocarbons present in AB asphaltenes.

TABLE 20

| Type of hydrocarbons | Percentage |
| --- | --- |
| Aliphatic | 90.39% |
| Aromatic | 9.61% |

Nitration in AH

Due to nitration of AH, the intensity of the prominent peaks of AH decreased, and there is a strong extra peak observed at 26.9036, which is possibly due to nitration.

Nitration in AB

In this spectrum there is no significant effect of nitration on AB; all the peaks represent AB only.

Nitration in AM

According to this spectrum, the intensity of the AM peaks was decreased due to nitration, and an extra strong peak observed at 26.9388 was possibly due to nitration.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A functionalized asphaltene represented by the formula:

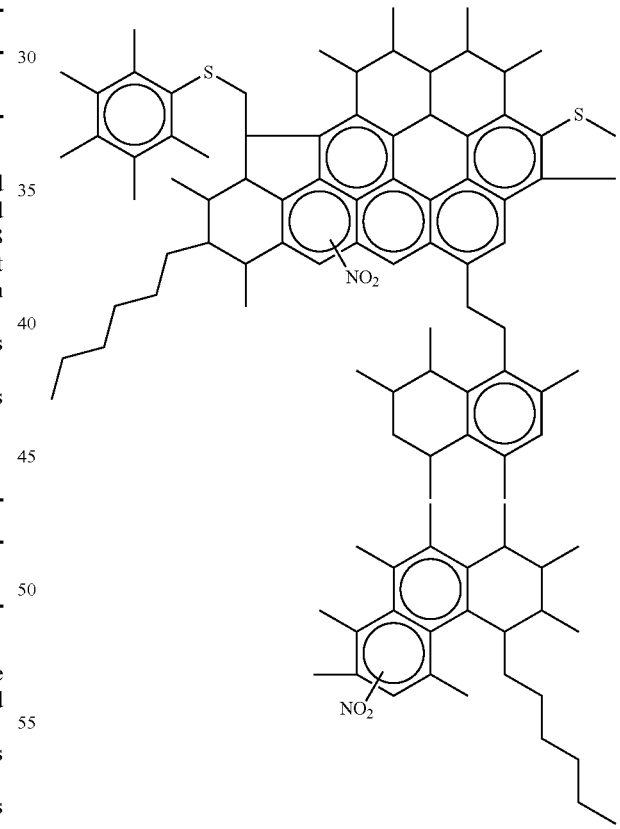

2. A method of preparing the functionalized asphaltene of claim 1, comprising:
mixing a crude asphaltene with sulfolane to form an asphaltene solution and cooling the asphaltene solution;
adding a nitric acid solution and a Lewis acid catalyst to the asphaltene solution then warming and stirring the asphaltene solution to form the nitrated asphaltene;

wherein the crude asphaltene is represented by the formula:

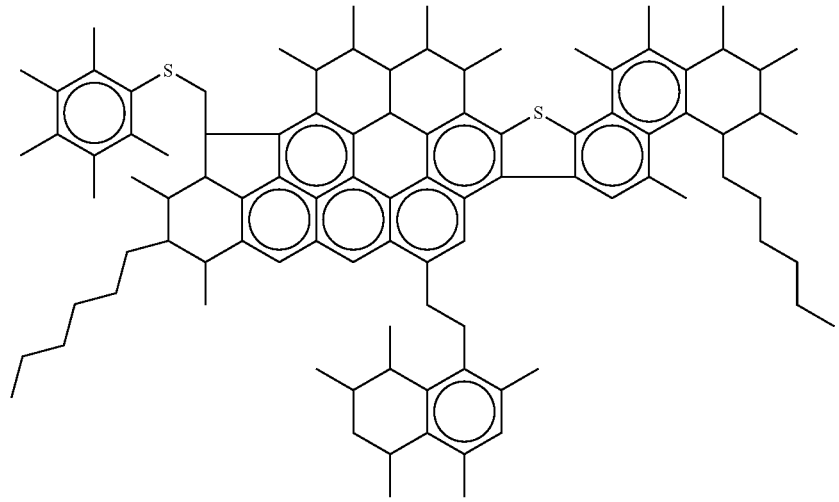

3. The method of claim 2, wherein the nitric acid solution is added to the asphaltene solution at between 5° C. and 15° C.

4. The method of claim 2, wherein the asphaltene is obtained from a Saudi Crude Oil selected from the group consisting of Arabia Extra Light (AB), Arabian Light (AL), Arabian Medium (AM) and Arabian Heavy (AH).

5. The method of claim 2, wherein the asphaltene is in a heavy hydrocarbon feed stream, the nitrated asphaltene is in a solid form and the method further comprises removing the nitrated asphaltene from the heavy hydrocarbon feed stream by precipitation.

6. A functionalized asphaltene represented by the formula:

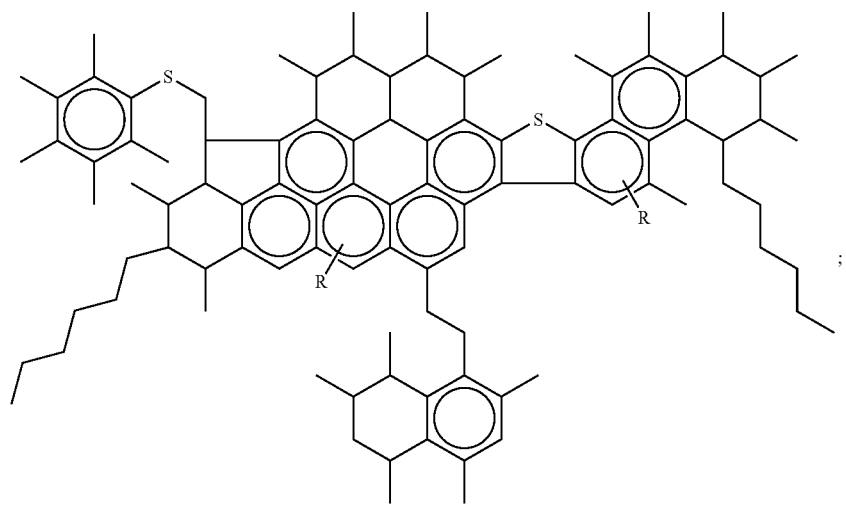

wherein each R is represented by a formula selected from the group consisting of:

7. A method of preparing the functionalized asphaltene of claim 6, comprising:

mixing an amine with water and hydrochloric acid to form an amine solution and cooling the amine solution;

displacing air in the amine solution;

mixing a sodium nitrite aqueous solution with the amine solution;

mixing a crude asphaltene with sulfolane to form an asphaltene solution an adding the asphaltene solution to the amine solution to form an amine-asphaltene mixture; and heating the amine-asphaltene mixture to form the functionalized asphaltene;

wherein:

the amine is selected from the group consisting of aniline, triethyl amine, t-butylamine, and piperidine; and the crude asphaltene is represented by the formula:

13. The method of claim 2, wherein the asphaltene solution has a concentration of 20-30 g/L (gram of the crude asphaltene per liter of the sulfolane).

14. The method of claim 2, wherein the asphaltene solution has a concentration of 25 g/L (gram of the crude asphaltene per liter of the sulfolane).

15. The method of claim 7, wherein the sodium nitrite solution is mixed with the amine solution when the amine solution has a temperature of 0° C.-5° C.

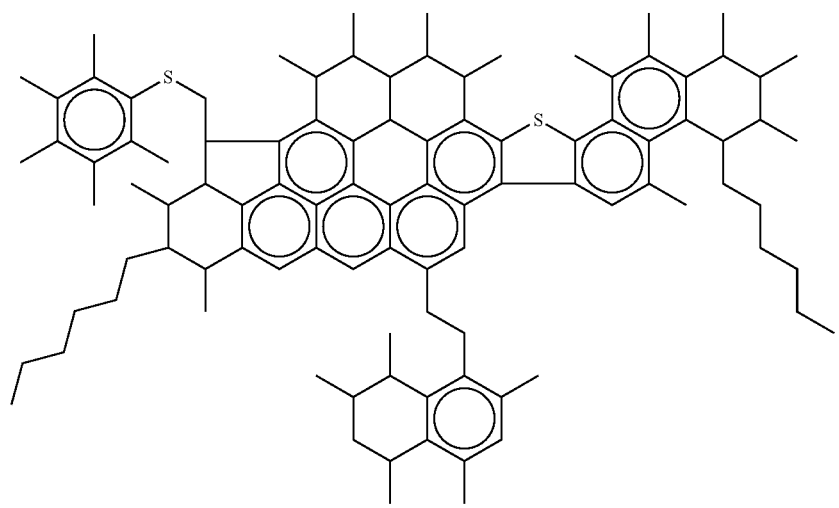

8. The method of claim 7, wherein the asphaltene is obtained from a Saudi Crude Oil selected from the group consisting of Arabia Extra Light (AB), Arabian Light (AL), Arabian Medium (AM) and Arabian Heavy (AH).

9. The method of claim 7, wherein the asphaltene is in a heavy hydrocarbon feed stream and the method further comprises solubilizing the functionalized asphaltene from the heavy hydrocarbon feed stream.

10. The method of claim 2, wherein the nitric acid solution comprises concentrated nitric acid and concentrated sulfuric acid at equal volumes.

11. The method of claim 2, wherein the asphaltene solution is cooled to 0° C.-10° C.

12. The method of claim 2, wherein the asphaltene solution is warmed to and stirred at room temperature.

16. The method of claim 7, wherein the amine solution has a concentration of 150-200 g/L (gram of the amine per liter of the water and the hydrochloric acid).

17. The method of claim 7, wherein the amine solution has a concentration of 187.5 g/L (gram of the amine per liter of the water and the hydrochloric acid).

18. The method of claim 7, wherein the sodium nitrite aqueous solution has a concentration of 300 g/L (gram of sodium nitrite per liter of water).

19. The method of claim 7, further comprising allowing the asphaltene-amine mixture to stand without cooling for 5 min under nitrogen before the heating.

\* \* \* \* \*